(12) United States Patent
Chaturvedi et al.

(10) Patent No.: US 10,583,293 B2
(45) Date of Patent: Mar. 10, 2020

(54) THERAPY PROGRAM SELECTION FOR ELECTRICAL STIMULATION THERAPY BASED ON A VOLUME OF TISSUE ACTIVATION

(71) Applicant: Medtronic, Inc., Minneapolis, MN (US)

(72) Inventors: Ashutosh Chaturvedi, Blaine, MN (US); Siddharth Dani, Minneapolis, MN (US); Timothy J. Denison, Minneapolis, MN (US); William F. Kaemmerer, Edina, MN (US); Shahram Malekkhosravi, Maple Grove, MN (US); Eric J. Panken, Edina, MN (US); Brandon Zingsheim, Circle Pines, MN (US)

(73) Assignee: Medtronic, Inc., Minneapolis, MN (US)

( * ) Notice: Subject to any disclaimer, the term of this patent is extended or adjusted under 35 U.S.C. 154(b) by 551 days.

(21) Appl. No.: 14/481,379

(22) Filed: Sep. 9, 2014

(65) Prior Publication Data

US 2016/0067495 A1 Mar. 10, 2016

(51) Int. Cl.
*A61B 5/0478* (2006.01)
*G16H 50/50* (2018.01)
(Continued)

(52) U.S. Cl.
CPC ........ *A61N 1/36128* (2013.01); *A61B 5/0478* (2013.01); *A61B 5/4064* (2013.01);
(Continued)

(58) Field of Classification Search
CPC ........ G06Q 10/00; G06Q 50/00; G16H 10/00; G16H 15/00; G16H 20/00; G16H 30/00;
(Continued)

(56) References Cited

U.S. PATENT DOCUMENTS

| | | |
|---|---|---|
| 7,346,382 B2 | 3/2008 | McIntyre et al. |
| 7,386,348 B2 | 6/2008 | North et al. |

(Continued)

FOREIGN PATENT DOCUMENTS

| | | |
|---|---|---|
| CN | 102089031 A | 6/2011 |
| CN | 102858406 A | 1/2013 |

(Continued)

OTHER PUBLICATIONS

International Search Report and Written Opinion from International Application No. PCT/US2015/026747, dated Jul. 23, 2015, 12 pp.

(Continued)

*Primary Examiner* — Robert W Morgan
*Assistant Examiner* — Charles P Coleman
(74) *Attorney, Agent, or Firm* — Shumaker & Sieffert, P.A.

(57) ABSTRACT

In some examples, a processor of a system evaluates a therapy program based on a score determined based on a volume of tissue expected to be activated ("VTA") by therapy delivery according to the therapy program. The score may be determined using an efficacy map comprising a plurality of voxels that are each assigned a value. In some examples, the efficacy map is selected from a plurality of stored efficacy maps based on a patient condition, one or more patient symptoms, or both the patient condition and one or more patient symptoms. In addition, in some examples, voxels of the efficacy map are assigned respective values that are associated with a clinical rating scale.

34 Claims, 9 Drawing Sheets

(51) Int. Cl.
*G16H 50/30* (2018.01)
*A61N 1/36* (2006.01)
*A61N 1/372* (2006.01)
*G06F 19/00* (2018.01)
*A61B 5/00* (2006.01)
*A61B 5/04* (2006.01)

(52) U.S. Cl.
CPC .......... *A61B 5/4833* (2013.01); *A61N 1/3605* (2013.01); *A61N 1/36067* (2013.01); *A61N 1/36082* (2013.01); *A61N 1/36096* (2013.01); *A61N 1/36132* (2013.01); *A61N 1/36182* (2013.01); *A61N 1/37247* (2013.01); *G06F 19/3481* (2013.01); *G16H 50/50* (2018.01); *A61B 5/04001* (2013.01); *A61B 5/4076* (2013.01); *G16H 50/30* (2018.01)

(58) Field of Classification Search
CPC ........ G16H 40/00; G16H 50/00; G16H 70/00; G16H 80/00; G16H 10/40; G16H 20/10; G16H 20/13; G16H 20/17; A61N 1/36128; A61N 1/36067; A61N 1/36082; A61N 1/36096; A61N 1/36132
USPC .................................................. 705/2, 3, 20
See application file for complete search history.

(56) References Cited

U.S. PATENT DOCUMENTS

| | | | |
|---|---|---|---|
| 7,623,918 B2 | 11/2009 | Goetz | |
| 7,657,319 B2 | 2/2010 | Goetz et al. | |
| 7,822,483 B2 | 10/2010 | Stone et al. | |
| 7,860,548 B2 | 12/2010 | McIntyre et al. | |
| 8,180,445 B1 | 5/2012 | Moffit | |
| 8,180,601 B2 | 5/2012 | Butson et al. | |
| 8,190,250 B2 | 5/2012 | Moffitt et al. | |
| 8,326,433 B2 | 12/2012 | Blum et al. | |
| 8,379,952 B2 | 2/2013 | McIntyre et al. | |
| 8,433,414 B2 | 4/2013 | Gliner et al. | |
| 8,515,549 B2 | 8/2013 | Panken et al. | |
| 8,886,332 B2 | 11/2014 | Molnar et al. | |
| 9,849,293 B2 | 12/2017 | Goetz | |
| 2006/0017749 A1* | 1/2006 | McIntyre | A61N 1/36082 345/664 |
| 2007/0083104 A1* | 4/2007 | Butson | A61N 1/0534 600/407 |
| 2007/0156451 A1* | 7/2007 | Gering | G06Q 10/00 705/2 |
| 2007/0203540 A1 | 8/2007 | Goetz et al. | |
| 2007/0225674 A1 | 9/2007 | Molnar et al. | |
| 2007/0276234 A1 | 11/2007 | Shahidi | |
| 2007/0288064 A1 | 12/2007 | Butson et al. | |
| 2008/0154341 A1 | 6/2008 | McIntyre et al. | |
| 2008/0269836 A1 | 10/2008 | Foffani et al. | |
| 2009/0016591 A1* | 1/2009 | Lakare | G06T 7/11 382/131 |
| 2009/0118610 A1 | 5/2009 | Karmarkar et al. | |
| 2009/0208703 A1 | 8/2009 | McIntyre et al. | |
| 2009/0281596 A1 | 11/2009 | King et al. | |
| 2009/0287271 A1* | 11/2009 | Blum | A61N 1/37247 607/45 |
| 2010/0042011 A1 | 2/2010 | Doidge et al. | |
| 2010/0049276 A1 | 2/2010 | Blum et al. | |
| 2010/0054563 A1* | 3/2010 | Mendonca | A61B 6/032 382/131 |
| 2010/0214318 A1 | 8/2010 | Pradeep et al. | |
| 2010/0241020 A1 | 9/2010 | Zaidel et al. | |
| 2010/0249538 A1 | 9/2010 | Pradeep et al. | |
| 2010/0256438 A1 | 10/2010 | Mishelevich et al. | |
| 2011/0040351 A1* | 2/2011 | Butson | G06F 19/345 607/59 |
| 2011/0040352 A1 | 2/2011 | Gerber et al. | |
| 2011/0093044 A1 | 4/2011 | Moffitt | |
| 2011/0093045 A1 | 4/2011 | Moffitt et al. | |
| 2011/0125078 A1 | 5/2011 | Denison et al. | |
| 2011/0184489 A1 | 7/2011 | Nicolelis et al. | |
| 2011/0191275 A1 | 8/2011 | Lujan et al. | |
| 2011/0218818 A1* | 9/2011 | Butson | G06F 19/345 705/2 |
| 2011/0307030 A1 | 12/2011 | John | |
| 2011/0307032 A1 | 12/2011 | Goetz et al. | |
| 2011/0313236 A1 | 12/2011 | Valente et al. | |
| 2012/0014580 A1 | 1/2012 | Blum et al. | |
| 2012/0116211 A1 | 5/2012 | McIntyre et al. | |
| 2012/0116475 A1 | 5/2012 | Nelson et al. | |
| 2012/0165898 A1* | 6/2012 | Moffitt | A61N 1/37247 607/45 |
| 2012/0197611 A1 | 8/2012 | Butson et al. | |
| 2012/0265267 A1 | 10/2012 | Blum et al. | |
| 2012/0302912 A1* | 11/2012 | Moffitt | A61N 1/36185 600/554 |
| 2012/0303087 A1* | 11/2012 | Moffitt | A61N 1/36185 607/45 |
| 2012/0303089 A1 | 11/2012 | Martens et al. | |
| 2012/0330622 A1* | 12/2012 | Butson | A61N 1/0534 703/1 |
| 2013/0030276 A1 | 1/2013 | McIntyre et al. | |
| 2013/0053722 A1 | 2/2013 | Carlson et al. | |
| 2013/0142411 A1* | 6/2013 | Da Silva | G06T 11/008 382/131 |
| 2013/0150922 A1* | 6/2013 | Butson | G06F 19/345 607/46 |
| 2013/0172716 A1 | 7/2013 | Lozano et al. | |
| 2013/0197605 A1 | 8/2013 | Carlson et al. | |
| 2013/0289380 A1* | 10/2013 | Molnar | A61N 1/36146 600/377 |
| 2013/0289660 A1 | 10/2013 | Molnar et al. | |
| 2014/0066999 A1* | 3/2014 | Carcieri | G06F 19/3406 607/2 |
| 2015/0088228 A1* | 3/2015 | Moffitt | A61N 1/37247 607/59 |

FOREIGN PATENT DOCUMENTS

| | | |
|---|---|---|
| WO | 2007097858 A1 | 8/2007 |
| WO | 2008070140 A2 | 6/2008 |
| WO | 2009137120 A1 | 11/2009 |
| WO | 2010120823 A2 | 10/2010 |
| WO | 2011025865 A1 | 3/2011 |
| WO | 2013012948 A1 | 1/2013 |

OTHER PUBLICATIONS

Buston, et al., "Sources and Effects of Electrode Impedance During Deep Brain Stimulation," Clinical Neurophysiology, 117, Dec. 22, 2005, 8 pp.
Cheung, et al., "Defining a Therapeutic Target for Pallidal Deep Brain Stimulation for Dystonia," American Neurological Association, May 20, 2014, 9 pp.
McIntyre, et al., "Cellular Effects of Deep Brain Stimulation: Model-Based Analysis of Activation and Inhibition," J. Neurophysiol, vol. 19, 2004, first published Dec. 10, 2003, pp. 1457-1469.
Beriault et al., "Towards Computer-Assisted Deep Brain Stimulation Targeting with Multiple Active Contacts," MICCAI International Conference on Medical Image Computing and Computer-Assisted Intervention, McConnell Brain Imagine Centre, Montreal Neurological Institute, Jan. 2012 8 pp.
Gross, et al., "The Clinical Utility of Methods to Determine Spatial Extent and Volume of Tissue Activated by Deep Brain Stimulation," Clinical Neurophisiology, vol. 119(9), Sep. 2008, pp. 1947-1950.
Carlson, et al., "Deep Brain Stimulation Does Not Silence Neurons in Subthalamic Nucleus in Parkinson's Patients," J Neurophysiol, 103, Dec. 2, 2009, pp. 962-967.
U.S. Appl. No. 14/195,489, filed Mar. 3, 2014, by Kaemmerer.
Examination Report from counterpart European Application No. 15723782.7, dated Nov. 27, 2018, 5 pp.
Response to Examination Report dated Nov. 27, 2018, from counterpart European Application No. 15723782.7, filed Apr. 5, 2019, 11 pp.

(56) References Cited

OTHER PUBLICATIONS

First Office Action and Search Report, and translation thereof, from counterpart Chinese Application No. 201580048312.2, dated May 28, 2019, 16 pp.

* cited by examiner

THERAPY PROGRAM SELECTION FOR ELECTRICAL STIMULATION THERAPY BASED ON A VOLUME OF TISSUE ACTIVATION

TECHNICAL FIELD

The disclosure relates to electrical stimulation therapy.

BACKGROUND

Implantable medical devices, such as electrical stimulators or therapeutic agent delivery devices, have been proposed for use in different therapeutic applications, such as deep brain stimulation (DBS), spinal cord stimulation (SCS), pelvic stimulation, gastric stimulation, peripheral nerve stimulation, functional electrical stimulation or delivery of pharmaceutical agent, insulin, pain relieving agent or anti-inflammatory agent to a target tissue site within a patient. In some therapy systems, an implantable electrical stimulator delivers electrical therapy to a target tissue site within a patient with the aid of one or more electrodes, which may be deployed by medical leads, on a housing of the electrical stimulator, or both.

During a programming session, which may occur during implant of the medical device, during a trial session, or during an in-clinic or remote follow-up session after the medical device is implanted in the patient, a clinician may generate one or more therapy programs (also referred to as therapy parameter sets) that provide efficacious therapy to the patient, where each therapy program may define values for a set of therapy parameters. A medical device may deliver therapy to a patient according to one or more stored therapy programs. In the case of electrical stimulation, the therapy parameters may define characteristics of the electrical stimulation waveform to be delivered. In examples in which electrical stimulation is delivered in the form of electrical pulses, for example, the therapy parameters may include an electrode combination, an amplitude, which may be a current or voltage amplitude, a pulse width, and a pulse rate.

SUMMARY

In general, the disclosure is directed to devices, systems, and methods for determining the therapeutic efficacy of a particular therapy program based on a volume of tissue expected to be activated by electrical stimulation delivered according to the therapy program. The volume of tissue expected to be activated by the electrical stimulation may also be referred to as a volume of tissue activation ("VTA"). In some examples, the therapeutic efficacy is indicated by a score that is determined based on a VTA generated based on the therapy program and an efficacy map. The efficacy map may be generated based on data specific to the particular patient for whom the therapy programs are being evaluated, or may be generated based on information from a plurality of patients.

In some examples, the efficacy map is a three-dimensional (3D) grid comprising a plurality of voxels that represent volumes of tissue. Some or all of the voxels may be assigned a value. In some examples, the values assigned to the voxels are associated with a clinical rating scale. For example, the values may be determined based on a retrospective study of a plurality patients receiving electrical stimulation therapy, and a clinical rating scale score for the patient that indicates the effects of the electrical stimulation therapy according to a therapy program. The value assigned to a particular voxel may be based on a combination of the clinical ratings score for each patient who received stimulation therapy that activated that voxel. In some examples, the clinical rating scale may be a clinical rating scale used to assess a patient condition with or without the presence of electrical stimulation therapy. In some examples, the efficacy map may be selected from a plurality of efficacy maps based on a patient condition or symptom. The efficacy maps may each quantify the effect of electrical stimulation on a different patient condition or symptom.

In some examples, a processor of a medical system may generate a VTA based on a therapy program, register the VTA with an efficacy map, and determine the efficacy score for the therapy program based on the values assigned to voxels of the efficacy map with which the VTA overlaps. For example, the efficacy score may be the sum of the values. The processor may select one or more therapy programs based on the efficacy scores determined in this manner.

In one example, the disclosure is directed to a method comprising generating, by a processor, a volume of tissue activation (VTA) based on a therapy program; selecting an efficacy map from a plurality of stored efficacy maps based on a patient condition or a patient symptom; and determining, based on the selected efficacy map, an efficacy score for the therapy program.

In another example, the disclosure is directed to a system including a memory configured to store a plurality of efficacy maps; and a processor configured to: generate a volume of tissue activation (VTA) based on a therapy program, select one of the plurality of efficacy maps based on a patient condition or a patient symptom, and determine, based on the selected efficacy map, an efficacy score for the therapy program.

In another example, the disclosure is directed to a method including generating, by a processor, a plurality of volume of tissue activations (VTAs) for a plurality of therapy programs, controlling a medical device to deliver electrical stimulation to a patient according to each of the therapy programs, receiving a clinical rating scale score for the patient for each of the therapy programs, associating each clinical rating scale score with each voxel of an efficacy map overlapped by the VTA corresponding to the therapy program resulting in the clinical rating scale score, and determining values for the plurality of voxels of the efficacy map based on the associated clinical rating scale scores.

In another example, the disclosure is directed to a system including a medical device configured to deliver stimulation to a patient according to each of a plurality of therapy programs, a user interface configured receive a clinical rating scale score for the patient for each of the plurality of therapy programs, and a processor configured to generate a plurality of volumes of tissue activations (VTAs) for each of the plurality of therapy programs, associate each clinical rating scale score with each voxel of an efficacy map overlapped by the VTA corresponding to the therapy program resulting in the clinical rating scale score, and determine values for the plurality of voxels of the efficacy map based on the associated clinical rating scales scores.

The details of one or more examples are set forth in the accompanying drawings and the description below. Other features, objects, and advantages will be apparent from the description and drawings, and from the claims.

DETAILED DESCRIPTION

Figure 1:
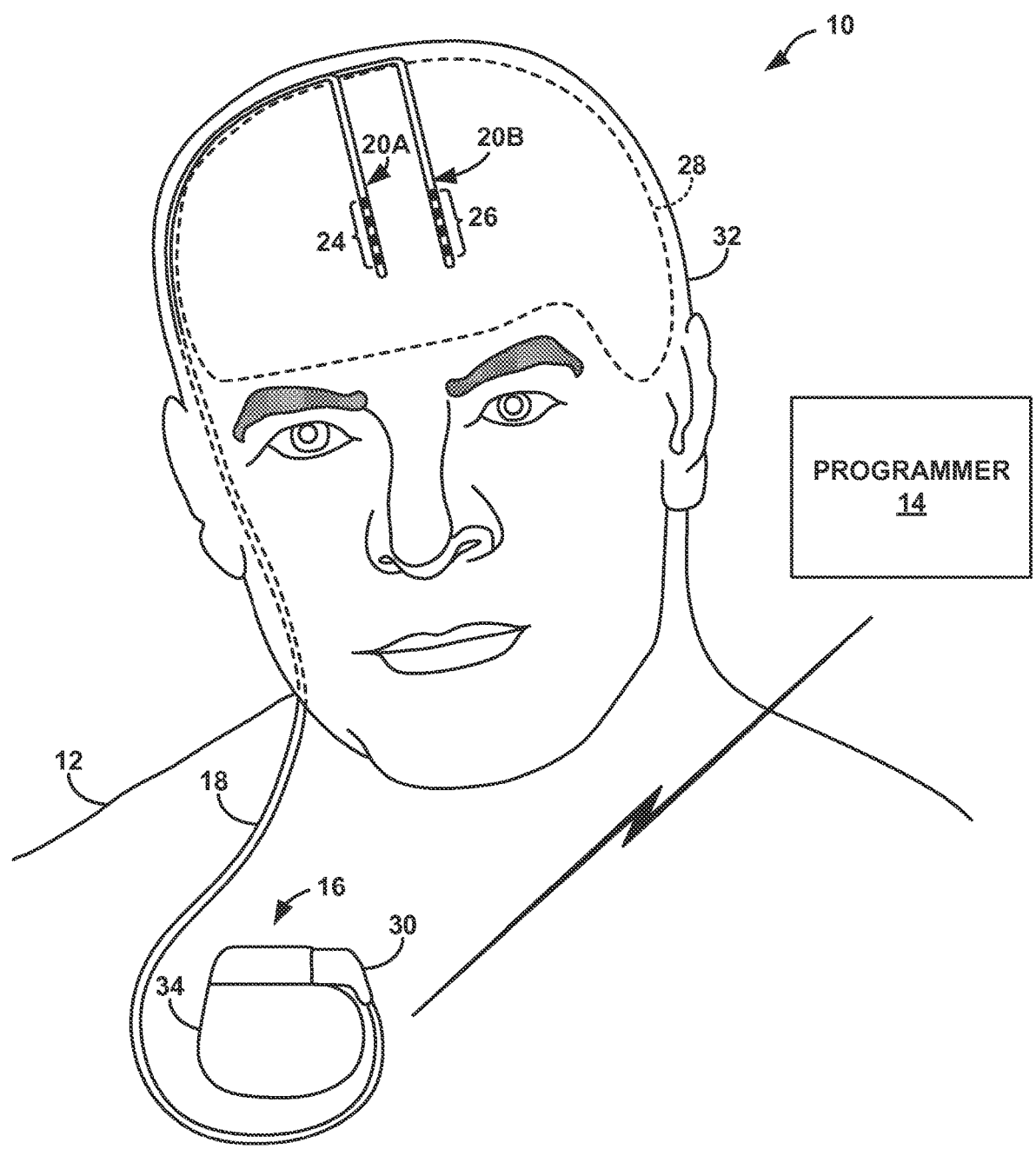
FIG. 1 is a conceptual diagram illustrating an example deep brain stimulation (DBS) system configured to deliver electrical stimulation therapy to a tissue site within a brain of a patient.

The present disclosure describes example devices, systems, and methods for quantifying the therapeutic efficacy of a particular therapy program based on a volume of tissue expected to be activated ("VTA") by electrical stimulation delivered via the therapy program. The quantifications of the therapeutic efficacy may be used to determine one or more therapy programs that may provide efficacious DBS to a patient. A therapy program may define, for example, values for one or more electrical stimulation parameters (e.g., frequency, current or voltage amplitude, and pulse width in the case of electrical stimulation pulses), an electrode combination (one or more electrodes selected to deliver electrical stimulation and the respective polarities), or both one or more electrical stimulation parameter values and the electrode combination. In some examples, tissue may be "activated" when the electrical stimulation causes an action potential to propagate along a neuron of the tissue, which may indicate that the transmembrane potential of the neuron reached a particular level, such as a potential greater than 0 millivolts (mV). A VTA may be determined for a particular therapy program (also referred to herein as a "set of electrical stimulation parameter values") using a modeling algorithm that is based on characteristics of the tissue of the patient proximate the one or more electrodes. In this way, the VTA may be estimated.

In some examples, the therapeutic efficacy of a particular therapy program is quantified by an efficacy score that is determined based on the VTA and an efficacy map. The efficacy map may be generated based on data specific to the particular patient for whom the therapy programs are being evaluated, or may be generated based on information from a plurality of patients. In some examples, the efficacy map may be selected (e.g., by a processor of a device) from a plurality of stored efficacy maps based on the patient condition, one or more patient symptoms, or both the patient condition and at least one symptom. The efficacy map may represent, for example, a volume of tissue (e.g., within a brain of a patient) known to provide efficacious results (e.g., a particular desired function) when activated, a volume of tissue known to provide adverse effects when activated, or a volume of tissue having mixed efficacious and adverse results.

In some examples, the efficacy map is a 3D grid comprising a plurality of voxels each representing a discrete volume of tissue. Some or all of the voxels may be assigned a value. In some examples, the value assigned to a voxel may be based on the function of the anatomical region represented by the voxel. For example, voxels representing tissue in a region of the patient associated with relatively high therapeutic efficacy when activated may be assigned a relatively high value, while voxels representing tissue in a region associated with relatively low therapeutic effect or adverse effects may be assigned a relatively low or even negative value.

In some examples, an efficacy map may provide a link between a VTA score and a clinical rating scale that a clinician may be familiar with. For example, the clinical rating scale may be the Unified Parkinson's Disease Rating Scale (UPDRS), the Yale-Brown Obsessive Compulsive Scale (YBOCS), the Hamilton Depression Rating Scale (HDRS), or the Burke-Fahn Marsden Dystonia Rating Scale (BFMDRS), for example. The rating scale appropriate for determining the therapeutic efficacy of one or more therapy programs may be based upon the patient condition and/or patient symptoms being treated via the electrical stimulation therapy. For example, UPDRS may be used when a patient is being treated for symptoms of Parkinson's disease, YBOCS may be used when the patient is being treated for Obsessive Compulsive Disorder (OCD), HDRS may be used when the patient is being treated for depression, and BFMDRS may be used when the patient is being treated for dystonia.

In some examples, a processor determines the values assigned to voxels of an efficacy map based on a clinical rating scale. For example, the values may be determined based on a retrospective study of a plurality of patients who received stimulation therapy. During the study, information may be collected for the plurality of patients, the information including therapy programs and the clinical rating scale scores associated with the therapeutic effect of the therapy program. The processor may receive the clinical rating scale scores and associate the clinical rating scores with the one or more voxels of an efficacy map with which a VTA generated based on the respective therapy program (associated with the clinical rating score) overlaps. In some examples, the value assigned to a particular voxel may be based on the clinical ratings scores associated with the particular voxel. For example, the value may be an average of the clinical rating scale scores, the highest of the associated clinical rating scale score, the lowest of the associated clinical rating scale scores, the median of the associated clinical rating scales scores, or a value based on any other algorithm using the associated clinical rating scale scores.

In other examples, the values for each voxel may be determined based on a single patient. For example, electrical stimulation may be applied to the patient according to a plurality of therapy programs. For each therapy program, a clinician may determine a clinical rating scale score characterizing the therapeutic effect of the therapy program, and a processor may associate the score with each voxel of the efficacy map with which the VTA resulting from the therapy program overlaps.

In some examples, a processor may be programmed to associate a change in clinical rating scale score between successive therapy programs with the voxels of the efficacy map that are either newly overlapped, or no longer overlapped by the VTA associated with the current therapy program. This may result in an efficacy map which more accurately corresponds to the additional functional value of a particular voxel within the efficacy map. For example, the processor may determine a change in overlap between a previous VTA and the efficacy map and the overlap of the current VTA and the efficacy map. The processor may assign the clinical rating scale score to each voxel associated with the change. In some examples, the clinical rating score may be assigned to each voxel of the efficacy map newly overlapped by the current VTA. In some examples, the processor may determine the amount of change between the clinical rating scale score associated with a previous VTA and the clinical rating scale score associated with the current VTA. The amount of change in the clinical rating scales score may be associated with each voxel that is different between the current VTA and the previous VTA within the efficacy map. In some examples, if the clinical rating scale score for the current VTA increased with respect to the previous VTA, then each voxel of the efficacy map newly overlapped by the VTA is associated with either the new clinical rating scales score, or a positive amount of change in the clinical rating scale score. If the previous VTA overlapped voxels of the efficacy map that are no longer overlapped by the current VTA, then those voxels may be associated with a negative value corresponding to the amount of change in the clinical ratings scale score. In some examples, the voxels that are no longer overlapped by be associated with the previous clinical rating scale score. If the clinical rating score has decreased, each voxel of the efficacy map newly overlapped by the VTA may be associated with the new clinical rating scale score or the negative amount of change in the clinical rating scale score. If the previous VTA overlapped voxels of the efficacy map that are no longer overlapped by the current VTA, then those voxels may be associated with a positive value corresponding to the amount of change in the clinical rating scale score. In some examples, the final value assigned to a particular voxel may be based on a combination of the rating scores for a plurality of VTAs which have been associated with the particular voxel. The combination may be an average, high, low, median or mean of the clinical rating scale scores, for example.

In some examples, a particular clinical rating scale may be combined with anatomical regions of a patient to create a clinical rating scale efficacy map (CRSEM), in which a voxel value is determined based on one or more clinical rating scale scores associated with the voxel and the anatomical region registered to the particular voxel. The efficacy map may be a result of assigning values to various voxels within an anatomical region based on the function of the anatomical region. As discussed above, in some examples, the clinical rating scale scores for each of a plurality of therapy programs may be used to describe the clinical benefit or function of anatomical regions of interest within the brain associated with a particular voxel when activated. For example, a value associated with a particular voxel describes a clinical benefit. In some examples, the clinical benefit for a particular voxel may be the average clinical rating scale score from the therapy programs, the maximum clinical rating scale score for the therapy programs, the lowest clinical rating scale score for the therapy programs, or a median of the clinical scores for the therapy programs.

In some examples, a CRSEM may include information that may used to generate an estimated clinical rating scale score for a therapy program, as well as one or more subscores directed to particular symptoms or functions. For example, a CRSEM associated with the UPDRS may also include subscores directed to speech, movement, and tremor control. In some examples, the subscores may take the form of quality of life point associated with a particular voxel. The quality of life points for a particular voxel may quantify how much that voxel contributes to the estimated UPDRS for a particular function. For example, areas of the CRSEM that overlap with parts of the brain associated with speech may have quality of life points, or another type of subscore, directed to quantifying the effect of activation of that area on speech.

In other examples, the CRSEM may be created retrospectively from a large number of patients. For example, information regarding a clinical rating scale score associated with a particular therapy program, along with the areas of the brain activated in association with the clinical rating scale score resulting from electrical stimulation according to the particular therapy program may be collected. The CRSEM may be generated based on the collected information. In addition, the CRSEM may be updated and improved incrementally by adding in new patient results. This may allow the algorithm used for generating scores based on the CRSEM to adapt the score intelligently. In some examples, the CRSEM data may be in a database which allows clinicians or researchers to determine brain regions of efficacy and side effects based on a large patient population. This may allow for the clinician or researcher to determine how electrical stimulation therapy may be adjusted based on a patient's particular disease state. This may allow for selection of various therapy programs based on the symptoms a particular patient is most interested in alleviating.

In some examples, a CRSEM created from prior patient data is used as a baseline during programming of a medical device to create a patient specific CRSEM. For example, a programmer may use a baseline CRSEM to select a subset of therapy programs based on estimated clinical scores from the CRSEM. During programming, a clinician may determine a patient-specific clinical rating scale score for the patient to quantify the therapeutic effect of therapy programs selected based on the baseline CRSEM. The clinician may input the estimated clinical rating scale scores into the programmer. The programmer may update the scores associated with each voxel of the CRSEM based on the patient-specific clinical rating scores. The programmer or the clinician may make programming selections of therapy programs based on the patient-specific CRSEM.

In some examples, a processor may use a baseline CRSEM based on prior patient data to generate a target VTA. The target VTA may represent a VTA corresponding to a relatively high efficacy score. In some examples, the target VTA may be generated based on an algorithm that takes into account considerations other than just high efficacy score, such as battery drain. In some examples, it may be a VTA corresponding to the highest achievable efficacy score based on an efficacy map. During programming, a processor implementing an algorithm may generate a VTA for each of a plurality of therapy programs and determine a score based on the comparison of the generated VTA to the target VTA. The plurality of therapy programs may be selected to provide coverage over a range of possible stimulation parameter values. The score may be based on the amount of overlap between the target VTA and the generated VTA. In some examples, the scoring function may, starting at a baseline, increase the score for generated VTA voxels that overlap with the target VTA and decrease the score for those voxels of the generated VTA that do not overlap the target VTA.

In some examples, the score may also be affected by overlap between the generated VTA and a brain atlas. For example, if certain areas within the target VTA are known to have a greater positive impact on a patient's clinical rating scale score, or overall therapeutic outcome of electrical stimulation therapy, overlap of a voxel with that area may be weighed more heavily in the final score for the generated VTA. Conversely, if a particular area within the brain is known to have a particularly adverse effect on clinical score or overall patient outcome the area of the efficacy map may have a negative effect on the score generated based on the efficacy map. In some examples, a plurality of therapy programs associated with the relatively highest scores may be used to deliver efficacious electrical stimulation therapy to the patient or for further testing on the patient.

For example, for each stimulation electrode combination of a plurality of electrode combinations, the stimulation parameter values resulting in the highest efficacy score may be stored in the patient programmer. In some examples, this may allow a patient to switch between high-scoring therapy programs as needed. For example, for a patient with Parkinson's disease, one electrode combination may provide electrical stimulation in an area of the brain associated with more efficacy results for speech. Switching to the highest scored program delivered by a set of electrodes near the portion of the brain responsible for speech may allow for a greater speech function for the patient. A separate electrode combination and corresponding therapy program may be selected by the patient when the patient intends to walk, for example. In other examples, the high scoring therapy programs may be selected based on which therapy programs provide the relatively highest result for each desired function. For example, a programmer may display the therapy program which maximizes speech function, the therapy program which maximizes movement, and the therapy program which minimizes tremor, and the patient may interact with the programmer to select one of the therapy programs. In response to receiving the input selecting one of the therapy programs, the programmer may control a medical device to deliver therapy to the patient in accordance with the selected therapy program.

In some examples, an efficacy map may be created for a particular disease, disease symptom, or desired function. The efficacy map may include each region of tissue (e.g., specifically anatomical structures of the brain) associated with either positive or negative effects of electrical stimulation therapy for the particular disease, symptom, or function. In some examples, each region within the efficacy map may be weighted differently based on how much the region contributes to the desired outcome.

In some examples, an efficacy score for a therapy program is generated based on the comparison of the VTA resulting from the therapy program to the efficacy map. In some examples, a processor generates an efficacy score for a plurality of therapy programs in order to determine a subset of therapy programs (e.g., specific electrode combinations) that may provide the most efficacious stimulation (within the plurality of tested therapy programs). In some examples, the most efficacious stimulation is defined as providing greatest therapeutic benefit with relatively minimal side effects. In some examples, an efficacy score based on an efficacy map may take into account both VTA overlap with patient anatomical regions as well as the function of the anatomical region that is overlapped. For example, a value associated with a voxel may incorporate both a portion attributed to the anatomical region, and a portion attributable to the function of that region. In some examples, the value associated with a voxel changes depending upon the desired outcome. For example, if the functional result of stimulation desired is minimizing tremor the value of a voxel may be one number, while if the functional result desired is maximizing movement, the value of the voxel may be another number. In some examples, the portion of the value associated with the anatomical region may stay the same, while the portion of the value associated with function may change.

In some examples, a programmer compares a generated VTA to an efficacy map for the brain to determine a score for the therapy program used to generate the VTA. For example, the VTA may be compared on a voxel by voxel level to the efficacy map. In some examples, voxels in different regions of tissue represented by the efficacy map may have different individual values. For example, for desirable regions, each voxel of overlap may add "one" to the overall efficacy score for the therapy program, while for undesirable regions each voxel of overlap may subtract "one" from the overall efficacy score of the therapy program. In some examples, some desirable regions may be weighted more heavily than others. For example, in certain regions of tissue associated with positive results when activated, each voxel of the efficacy grid corresponding to the regions and overlapped by the VTA may add 2 or 3 to the overall score. Similarly, voxels of the efficacy map corresponding to regions of tissue found to have particularly negative effects on overall patient state when activated may result in a decrease of a greater amount from the overall efficacy score when the VTA overlaps with such voxels. In some examples, the value for a particular voxel may be adjusted based on patient feedback. In some examples, both the efficacy score for the therapy program and an estimated clinical rating scale score for the therapy program may be displayed to a clinician.

The quantification of the therapeutic efficacy using the devices, systems, and techniques disclosed herein may help improve accuracy and efficiency of post-operative device programming for deep brain stimulation (DBS). For example, the efficacy scores determined using the techniques disclosed herein may be used to determine one or more therapy programs that provide effective therapy to a patient while minimizing side effects.

FIG. 1 is a conceptual diagram illustrating an example therapy system 10 that is configured to deliver therapy to patient 12 to manage a disorder of patient 12. Patient 12 ordinarily will be a human patient. In some cases, however, therapy system 10 may be applied to other mammalian or non-mammalian non-human patients. In the example shown in FIG. 1, therapy system 10 includes medical device programmer 14, implantable medical device (IMD) 16, lead extension 18, and one or more leads 20A and 20B (collectively "leads 20") with respective sets of electrodes 24, 26. IMD 16 includes a stimulation generator configured to generate and deliver electrical stimulation therapy to one or more regions of brain 28 of patient 12 via one or more electrodes 24, 26 of leads 20A and 20B, respectively.

In the example shown in FIG. 1, therapy system 10 may be referred to as a deep brain stimulation (DBS) system because IMD 16 is configured to deliver electrical stimulation therapy directly to tissue within brain 28, e.g., a tissue site under the dura mater of brain 28 or one or more branches or nodes, or a confluence of fiber tracks. In other examples, leads 20 may be positioned to deliver therapy to a surface of brain 28 (e.g., the cortical surface of brain 28). For example, in some examples, IMD 16 may provide cortical stimulation therapy to patient 12, e.g., by delivering electrical stimulation to one or more tissue sites in the cortex of brain 28. As another example, IMD 16 may provide vagal nerve stimulation (VNS) therapy to patient 12 by delivering electrical stimulation to one or more vagal nerve tissue sites.

DBS may be used to treat or manage various patient conditions, such as, but not limited to, seizure disorders (e.g., epilepsy), pain, migraine headaches, psychiatric disorders (e.g., major depressive disorder (MDD), bipolar disorder, anxiety disorders, post traumatic stress disorder, dysthymic disorder, and obsessive compulsive disorder (OCD)), behavior disorders, mood disorders, memory disorders, mentation disorders, movement disorders (e.g., essential tremor or Parkinson's disease), Huntington's disease, Alzheimer's disease, or other neurological or psychiatric disorders and impairment of patient 12.

Therapy systems configured for treatment of other patient conditions via delivery of therapy to brain 28 or another suitable target therapy delivery site in patient 12 can also be used in accordance with the techniques for determining one or more efficacy maps as disclosed herein. For example, in other applications of therapy system 10, the target therapy delivery site within patient 12 may be a location proximate to a spinal cord or sacral nerves (e.g., the S2, S3 or S4 sacral nerves) in patient 12 or any other suitable nerve, organ, muscle or muscle group in patient 12, which may be selected based on, for example, a patient condition. For example, therapy system 10 may be used to deliver electrical stimulation or a therapeutic agent to tissue proximate to a pudendal nerve, a perineal nerve or other areas of the nervous system, in which cases, leads 20 would be implanted and substantially fixed proximate to the respective nerve. As further examples, an electrical stimulation system may be positioned to deliver a stimulation to help manage peripheral neuropathy or post-operative pain mitigation, ilioinguinal nerve stimulation, intercostal nerve stimulation, gastric stimulation for the treatment of gastric mobility disorders and obesity, muscle stimulation, for mitigation of other peripheral and localized pain (e.g., leg pain or back pain).

In the example shown in FIG. 1, IMD 16 may be implanted within a subcutaneous pocket in the pectoral region of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 28. IMD 16 can be constructed of a biocompatible material that resists corrosion and degradation from bodily fluids. IMD 16 may comprise a hermetic housing 34 to substantially enclose components, such as a processor, a therapy module, and memory.

In the example shown in FIG. 1, leads 20 are implanted within the right and left hemispheres, respectively, of brain 28 in order to deliver electrical stimulation to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere at multiple target tissue sites or IMD 16 may be coupled to a single lead that is implanted in one or both hemispheres of brain 28.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 via any suitable technique, such as through respective burr holes in the skull of patient 12 or through a common burr hole in the cranium 32. Leads 20 may be placed at any location within brain 28 such that electrodes 24, 26 are capable of providing electrical stimulation to target therapy delivery sites within brain 28 during treatment. Different neurological or psychiatric disorders may be associated with activity in one or more of regions of brain 28, which may differ between patients. Accordingly, the target therapy delivery site for electrical stimulation therapy delivered by leads 20 may be selected based on the patient condition. For example, a suitable target therapy delivery site within brain 28 for controlling a movement disorder of patient 12 may include one or more of the pedunculopontine nucleus (PPN), thalamus, basal ganglia structures (e.g., globus pallidus, substantia nigra or subthalamic nucleus), zona inserta, fiber tracts, lenticular fasciculus (and branches thereof), ansa lenticularis, or the Field of Forel (thalamic fasciculus). The PPN may also be referred to as the pedunculopontine tegmental nucleus.

As another example, in the case of MDD, bipolar disorder, OCD, or other anxiety disorders, leads 20 may be implanted to deliver electrical stimulation to the anterior limb of the internal capsule of brain 28, and only the ventral portion of the anterior limb of the internal capsule (also referred to as a VC/VS), the subgenual component of the cingulate cortex (which may be referred to as CG25), anterior cingulate cortex Brodmann areas 32 and 24, various parts of the prefrontal cortex, including the dorsal lateral and medial pre-frontal cortex (PFC) (e.g., Brodmann area 9), ventromedial prefrontal cortex (e.g., Brodmann area 10), the lateral and medial orbitofrontal cortex (e.g., Brodmann area 11), the medial or nucleus accumbens, thalamus, intralaminar thalamic nuclei, amygdala, hippocampus, the lateral hypothalamus, the Locus ceruleus, the dorsal raphe nucleus, ventral tegmentum, the substantia nigra, subthalamic nucleus, the inferior thalamic peduncle, the dorsal medial nucleus of the thalamus, the habenula, the bed nucleus of the stria terminalis, or any combination thereof.

As another example, in the case of a seizure disorder or Alzheimer's disease, for example, leads 20 may be implanted to deliver electrical stimulation to regions within the Circuit of Papez, such as, e.g., one or more of the anterior thalamic nucleus, the internal capsule, the cingulate, the fornix, the mammillary bodies, the mammillothalamic tract (mammillothalamic fasciculus), or the hippocampus. Target therapy delivery sites not located in brain 28 of patient 12 are also contemplated.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

In the examples shown in FIG. 1, electrodes 24, 26 of leads 20 are shown as ring electrodes. Ring electrodes may be relatively easy to program and may be capable of delivering an electrical field to any tissue adjacent to leads 20. In other examples, electrodes 24, 26 of leads 20 may have different configurations. For example, one or more of the electrodes 24, 26 of leads 20 may have a complex electrode array geometry that is capable of producing shaped electrical fields, including interleaved stimulation. An example of a complex electrode array geometry may include an array of electrodes positioned at different axial positions along the length of a lead, as well as at different angular positions about the periphery, e.g., circumference, of the lead. The complex electrode array geometry may include multiple electrodes (e.g., partial ring or segmented electrodes) around the perimeter of each lead 20, in addition to, or instead of, a ring electrode. In this manner, electrical stimulation may be directed to a specific direction from leads 20 to enhance therapy efficacy and reduce possible adverse side effects from stimulating a large volume of tissue.

In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. In other examples, leads 20 may have shapes other than elongated cylinders as shown in FIG. 1 with active or passive tip configurations. For example, leads 20 may be paddle leads, spherical leads, bendable leads, or any other type of shape effective in treating patient 12.

IMD 16 may deliver electrical stimulation therapy to brain 28 of patient 12 according to one or more stimulation therapy programs (also referred to herein as "set of stimulation parameter values"). A stimulation therapy program may define one or more electrical stimulation parameter values for therapy generated by a stimulation generator of IMD 16 and delivered from IMD 16 to a target therapy delivery site within patient 12 via one or more electrodes 24, 26. The electrical stimulation parameters may define an aspect of the electrical stimulation therapy, and may include, for example, voltage or current amplitude of an electrical stimulation signal, a charge level of an electrical stimulation, a frequency of the electrical stimulation signal, waveform shape, on/off cycling state (e.g., if cycling is "off", stimulation is always on, and if cycling is "on", stimulation is cycled on and off) and, in the case of electrical stimulation pulses, pulse rate, pulse width, and other appropriate parameters such as duration or duty cycle. In addition, if different electrodes are available for delivery of stimulation, a therapy parameter of a therapy program may be further characterized by an electrode combination, which may define selected electrodes 24, 26 and their respective polarities. In some examples, stimulation may be delivered using a continuous waveform and the stimulation parameters may define this waveform.

In addition to being configured to deliver therapy to manage a disorder of patient 12, therapy system 10 may be configured to sense bioelectrical brain signals or another physiological parameter of patient 12. For example, IMD 16 may include a sensing module that is configured to sense bioelectrical brain signals within one or more regions of brain 28 via a subset of electrodes 24, 26, another set of electrodes, or both. Accordingly, in some examples, electrodes 24, 26 may be used to deliver electrical stimulation from the therapy module to target sites within brain 28 as well as sense brain signals within brain 28. However, IMD 16 can also use a separate set of sensing electrodes to sense the bioelectrical brain signals. In some examples, the sensing module of IMD 16 may sense bioelectrical brain signals via one or more of the electrodes 24, 26 that are also used to deliver electrical stimulation to brain 28. In other examples, one or more of electrodes 24, 26 may be used to sense bioelectrical brain signals while one or more different electrodes 24, 26 may be used to deliver electrical stimulation.

External medical device programmer 14 is configured to wirelessly communicate with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. In addition, or instead, programmer 14 may be a patient programmer that allows patient 12 to select programs and/or view and modify therapy parameter values. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device, voice activation, or another input mechanism that allows the user to navigate though the user interface of programmer 14 and provide input. If programmer 14 includes buttons and a keypad, the buttons may be dedicated to performing a certain function, e.g., a power button, the buttons and the keypad may be soft keys that change in function depending upon the section of the user interface currently viewed by the user, or any combination thereof.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit programming information to IMD 16. Programming information may include, for example, hardware information, such as the type of leads 20, the arrangement of electrodes 24, 26 on leads 20, the position of leads 20 within brain 28, one or more therapy programs defining therapy parameter values, therapeutic windows for one or more electrodes 24, 26, and any other information that may be useful for programming into IMD 16. Programmer 14 may also be capable of completing functional tests (e.g., measuring the impedance of electrodes 24, 26 of leads 20).

The clinician may also generate and store therapy programs within IMD 16 with the aid of programmer 14. Programmer 14 may assist the clinician in the creation/identification of therapy programs by providing a system for identifying potentially beneficial therapy parameter values. For example, during a programming session, programmer 14 may generate a VTA for each therapy program of a plurality of therapy programs. In some examples, at least some of the therapy programs may have the same electrode combination (but different values of at least one other therapy parameter) and these therapy programs may be organized into subsets, each subset having the same electrode combination. A processor of programmer 14 may select the most efficacious therapy program for each subset and display a list of the selected therapy programs. The clinician may select a therapy program from the list to provide therapy to patient 12 to address symptoms associated with the patient condition.

As discussed in further detail below, in some examples, programmer 14 (or another computing device) is configured to determine, for at least one therapy program delivered by therapy system 10, an efficacy score. The therapy program may include for example, an electrode combination, a stimulation amplitude, a stimulation pulse width, and a stimulation frequency. In some examples, the score may be an efficacy score determined based on a clinical rating scale efficacy map (CRSEM). In some examples, the efficacy score may be an estimated clinical rating scale score. The CRSEM may be patient specific. In some examples, the patient-specific CRSEM may be based on a baseline CRSEM created retrospectively based on a large number of patients, and then updated based on a patient's response to stimulation and/or patient-specific brain structures.

In some examples, the CRSEM may be used to generate a target VTA. A score for a particular therapy program may be determined based on the comparison between a VTA generated based on the therapy program and the target VTA. In some examples, the target VTA may be based on a combination of the CRSEM and regions of interest within the brain. The regions of interest may be based on a patient specific brain anatomy map that identifies target brain nuclei relevant to DBS, for example. The target VTA may include areas that overlap the regions of interest resulting in a high estimated clinical rating score. In some examples, programmer 14 may compare therapy programs, and generate and display information regarding the VTAs for each therapy program. For example, programmer 14 may generate a display that lists each electrode 24, 26, or a subset of electrodes 24, 26, and, for each electrode or electrode combination, the therapy program(s) resulting in the highest score. In some examples, the estimated clinical rating scale score may be displayed.

In some examples, the CRSEM may be used to adjust a score based on a comparison of a generated VTA to various regions of interest within the brain. For example, the generated VTA may be compared to an efficacy map on a voxel by voxel basis. Each comparison may affect the overall score for the generated VTA.

In some examples, estimated clinical rating scale scores may be determined before leads 20 are implanted in patient 12, e.g., pre-operatively. For example, the estimated clinical rating scale scores may be determined based on the expected implantation site of leads 20 in patient 12. In these examples, the estimated clinical ratings scale scores for a plurality of VTAs may be determined based on CRSEMs determined, in part, by using images of patient 12 (e.g., based on a brain atlas specific to patient 12), such that the information identifying estimated clinical scores for each of the electrodes 24, 26 may be specifically tailored to patient 12. The target location of leads 20 and electrodes 24, 26 may be selected and modeled, e.g., by a processor of programmer 14, in order to determine the VTAs expected to result from delivery of electrical stimulation by select electrode(s) 24, 26 of leads 20 if leads 20 were implanted in patient 12. In addition, programmer 14 (or another device) may determine estimated clinical rating scale scores based on different target locations for electrodes 24, 26, e.g., in order to pre-operatively select an actual implant site for leads 20. During implantation of lead 16 within patient 12, a clinician may attempt to position electrodes 24, 26 of leads 20 close to or within a target anatomical region. The anatomical region within patient 12 that serves as the target tissue site for stimulation delivered by IMD 14 may be selected based on the patient condition. For example, stimulating particular structures of brain 18, such as the Substantia Nigra, may help reduce the number and magnitude of tremors experienced by patient 12. Other anatomical regions for DBS may include the subthalamic nucleus, globus pallidus interna, ventral intermediate, and zona inserta. In other examples, processor 14 may, for example, select the implant site that results in the relatively highest estimated clinical rating scale scores or the relatively greatest number of electrodes associated with estimated clinical rating scale scores greater than or equal to a predetermined threshold.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12.

Whether programmer 14 is configured for clinician or patient use, programmer 14 is configured to communicate with IMD 16 and, optionally, another computing device, via wireless communication. Programmer 14, for example, may communicate via wireless communication with IMD 16 using radio frequency (RF) and/or inductive telemetry techniques known in the art, which may comprise techniques for proximal, mid-range, or longer-range communication. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

System 10 shown in FIG. 1 is merely one example of a therapy system for which an efficacy score may be determined for one or more therapy programs. The techniques described herein can be used to determine the therapy programs resulting in high efficacy scores of other therapy systems, such as therapy systems with other configurations of leads and electrodes, therapy systems with more than one IMD, and therapy systems including one or more leadless electrical stimulators (e.g., microstimulators having a smaller form factor than IMD 16 and which may not be coupled to any separate leads). The leadless electrical stimulators can be configured to generate and deliver electrical stimulation therapy to patient 12 via one or more electrodes on an outer housing of the electrical stimulator.

While DBS may successfully reduce symptoms of some neurological diseases, the stimulation may also cause unwanted side effects, also referred to herein as adverse effects. Side effects may include incontinence, tingling, loss of balance, paralysis, slurred speech, loss of memory, loss of inhibition, and many other neurological problems. Side effects may be mild to severe. DBS may cause one or more adverse effects by inadvertently providing electrical stimulation pulses to anatomical regions near the targeted anatomical region. These anatomical regions may be referred to as regions associated with adverse stimulation effects. For this reason, a clinician may program IMD 16 with a therapy program (or a plurality of therapy programs) that defines stimulation parameter values that balance effective therapy and minimize side effects.

With the aid of programmer 14 or another computing device, a clinician may select values for therapy parameters for therapy system 10, including an electrode combination. By selecting particular electrodes 24, 26 for delivering electrical stimulation therapy to patient 12, a clinician may modify the electrical stimulation therapy to target one or more particular regions of tissue (e.g., specific anatomical structures) within brain 28 and avoid other regions of tissue within brain 28. In addition, by selecting values for the other stimulation parameter values that define the electrical stimulation signal, e.g., the amplitude, pulse width, and pulse rate, the clinician may generate an efficacious therapy for patient 12 that is delivered via the selected electrode subset. Due to physiological diversity, condition differences, and inaccuracies in lead placement, the parameter values may vary between patients.

During a programming session, the clinician may determine one or more therapy programs that may provide effective therapy to patient 12. Patient 12 may provide feedback to the clinician as to the efficacy of the specific program being evaluated, which may include information regarding adverse effects of delivery of therapy according to the specific program. In some examples, the patient feedback may be used to determine a clinical rating scale score. Once the clinician has identified one or more programs that may be beneficial to patient 12, patient 12 may continue the evaluation process and determine which program best alleviates the condition of patient 12 or otherwise provides efficacious therapy to patient 12. Programmer 14 may assist the clinician in the creation/identification of therapy programs by providing a methodical system of identifying potentially beneficial therapy parameters.

In some examples described herein, a processor of therapy system 10 (e.g., a processor of IMD 16 or programmer 14) is configured to automatically determine at least one of an efficacy score or an estimated clinical rating scale score for a therapy program based on a VTA expected to result from electrical stimulation delivered according to the therapy program. In examples, the processor may determine an efficacy score for a therapy program that includes stimulation delivered via an electrode configuration closest to a target location. The efficacy score or estimated clinical rating scale scores is determined using computer modeling, rather than based on the results of actual electrical stimulation delivered to patient 12 by IMD 16 with the selected stimulation parameter values. Thus, in some examples, the processor may determine the stimulation parameters values which are most likely to maximize patient outcome without patient 12 being present in a clinic, which may help reduce the amount of time patient 12 is required to be in the clinic in order to program IMD 16. In addition, in some examples, efficacy scores or clinical rating scale scores may be estimated prior to implanting leads 20 in patient 12, which may provide a starting point for programming electrical stimulation parameters for IMD 16 after implanting leads 20 in patient 12.

As described in further detail below, in some examples, programmer 14 determines at least one of an efficacy score or an estimated clinical rating scale score for each of a plurality of therapy programs based on a volume of tissue expected to be activated by electrical stimulation delivered according to the therapy program. Programmer 14 may be configured to generate the VTA for a therapy program using any suitable technique, such as any one of the techniques described below with respect to FIG. 4. In some examples, a processor of programmer 14 automatically determines at least one of an efficacy score or an estimated clinical rating scale score for a therapy program by comparing the VTA to an efficacy map. In some examples, the VTA expected to result from the delivery of electrical stimulation according to a set of electrical stimulation parameter values is compared to a CRSEM to generate an estimated clinical rating scale score. The efficacy score or the estimated clinical rating scale score may take into account whether the VTA overlaps with an area of the brain known to result in adverse-effects when stimulated.

In some examples, generating an efficacy score or estimated clinical ratings score may include providing different weights to various efficacy regions and different adverse-effects regions of the patient. In such examples, the maximum score may not occur when the VTA first overlaps with one or more adverse-effects regions. In other examples, the efficacy score or the estimated clinical rating scale score may include a plurality of subscores, where each subscore may correspond to a different desired efficacious outcome. For example, for a patient with Parkinson's disease, one subscore may quantify efficacy of stimulation in facilitating movement, another may quantify efficacy of stimulation in minimizing tremor, and third may quantify efficacy in facilitating speech.

After determining the efficacy scores and/or estimated clinical rating scale scores for each of a plurality of therapy programs, the processor of programmer 14 may store the maximum scores with an indication of the therapy program, and the electrode combination used to delivery the therapy program. In some examples, programmer 14 generates and presents a display that includes a list of a plurality of electrodes and respective maximum scores and therapy programs, or any combination thereof.

Figure 2:
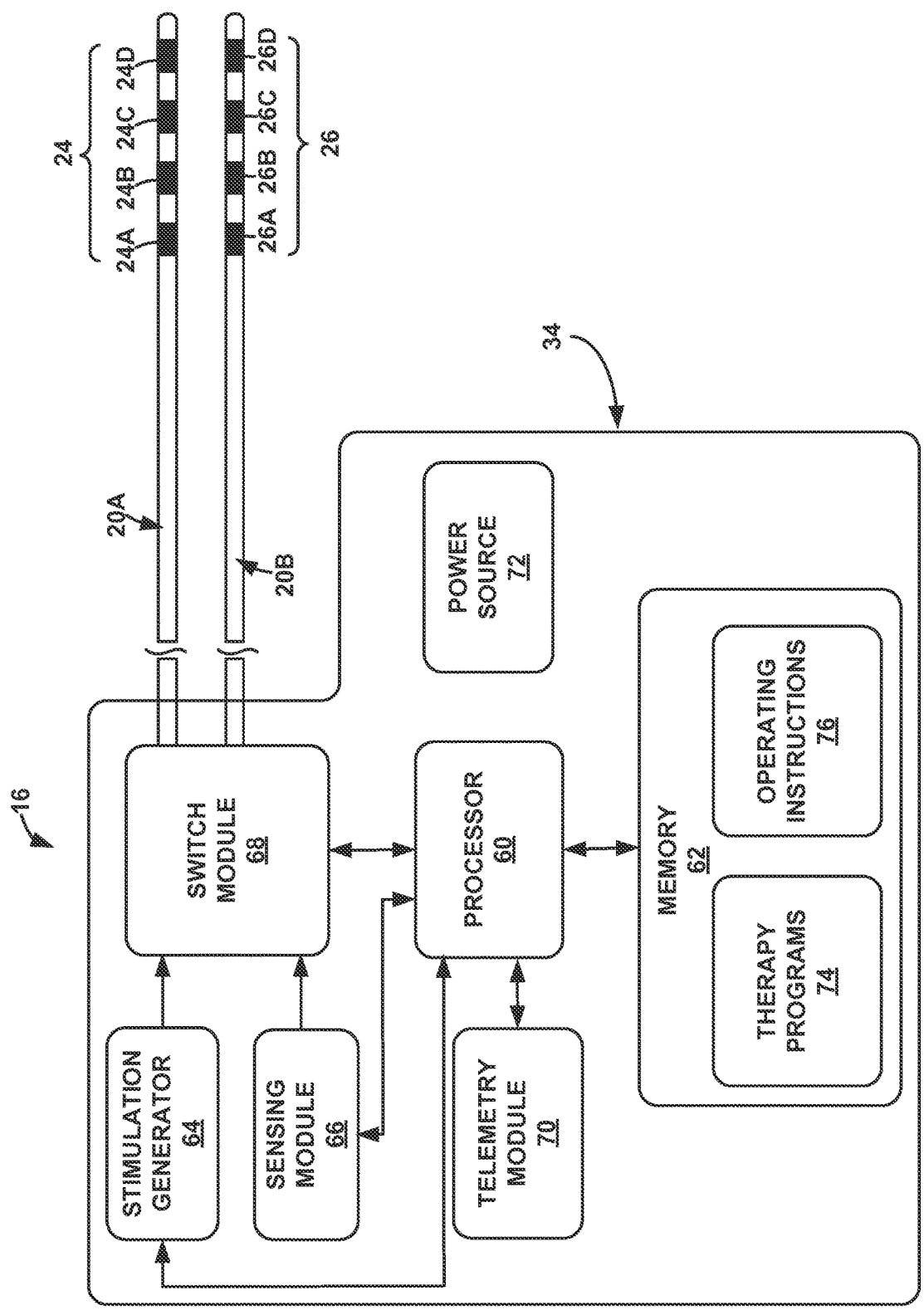
FIG. 2 is functional block diagram illustrating components of an example medical device.

FIG. 2 is functional block diagram illustrating components of an example IMD 16. In the example shown in FIG. 2, IMD 16 includes processor 60, memory 62, stimulation generator 64, sensing module 66, switch module 68, telemetry module 70, and power source 72. Memory 62, as well as other memories described herein, may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processor 60, cause IMD 16 to perform various functions described herein.

In the example shown in FIG. 2, memory 62 stores therapy programs 74 and operating instructions 76, e.g., in separate memories within memory 62 or separate areas within memory 62. Each stored therapy program 74 defines a particular program of therapy in terms of respective values for electrical stimulation parameters, such as an electrode combination, current or voltage amplitude, and, if stimulation generator 64 generates and delivers stimulation pulses, the therapy programs may define values for a pulse width, and pulse rate of a stimulation signal. Each stored therapy program 74 may also be referred to as a set of stimulation parameter values. Operating instructions 76 guide general operation of IMD 16 under control of processor 60, and may include instructions for monitoring brain signals within one or more brain regions via electrodes 24, 26 and delivering electrical stimulation therapy to patient 12.

Stimulation generator 64, under the control of processor 60, generates stimulation signals for delivery to patient 12 via selected combinations of electrodes 24, 26. In some examples, stimulation generator 64 generates and delivers stimulation signals to one or more target regions of brain 28 (FIG. 1), via a selected combination of electrodes 24, 26, based on one or more stored therapy programs 74. The target tissue sites within brain 28 for stimulation signals or other types of therapy and stimulation parameter values may depend on the patient condition for which therapy system 10 is implemented to manage. While stimulation pulses are described, stimulation signals may be of any form, such as continuous-time signals (e.g., sine waves) or the like.

The processors described in this disclosure, including processor 60, may include one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. Processor 60 is configured to control stimulation generator 64 according to therapy programs 74 stored by memory 62 to apply particular stimulation parameter values specified by one or more programs, such as amplitude, pulse width, and pulse rate.

In the example shown in FIG. 2, the set of electrodes 24 of lead 20A includes electrodes 24A, 24B, 24C, and 24D, and the set of electrodes 26 of lead 20B includes electrodes 26A, 26B, 26C, and 26D. Processor 60 may control switch module 68 to apply the stimulation signals generated by stimulation generator 64 to selected combinations of electrodes 24, 26. In particular, switch module 68 may couple stimulation signals to selected conductors within leads 20, which, in turn, deliver the stimulation signals across selected electrodes 24, 26. Switch module 68 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 64 is coupled to electrodes 24, 26 via switch module 68 and conductors within leads 20. In some examples, however, IMD 16 does not include switch module 68.

Stimulation generator 64 may be a single channel or multi-channel stimulation generator. In particular, stimulation generator 64 may be capable of delivering a single stimulation pulse, multiple stimulation pulses or continuous signal at a given time via a single electrode combination or multiple stimulation pulses at a given time via multiple electrode combinations. In some examples, however, stimulation generator 64 and switch module 68 may be configured to deliver multiple channels on a time-interleaved basis. For example, switch module 68 may serve to time divide the output of stimulation generator 64 across different electrode combinations at different times to deliver multiple programs or channels of stimulation energy to patient 12.

Sensing module 66, under the control of processor 60, is configured to sense bioelectrical brain signals of patient 12 via a selected subset of electrodes 24, 26 or with one or more electrodes 24, 26 and at least a portion of a conductive outer housing 34 of IMD 16, an electrode on an outer housing of IMD 16 or another reference. Processor 60 may control switch module 68 to electrically connect sensing module 66 to selected electrodes 24, 26. In this way, sensing module 66 may selectively sense bioelectrical brain signals with different combinations of electrodes 24, 26 (and/or a reference other than an electrode 24, 26).

Although sensing module 66 is incorporated into a common housing 34 with stimulation generator 64 and processor 60 in FIG. 2, in other examples, sensing module 66 is in a separate outer housing from outer housing 34 of IMD 16 and communicates with processor 60 via wired or wireless communication techniques.

Telemetry module 70 is configured to support wireless communication between IMD 16 and an external programmer 14 or another computing device under the control of processor 60. Processor 60 of IMD 16 may receive, as updates to programs, values for various stimulation parameters such as amplitude and electrode combination, from programmer 14 via telemetry module 70. The updates to the therapy programs may be stored within therapy programs 74 portion of memory 62. Telemetry module 70 in IMD 16, as well as telemetry modules in other devices and systems described herein, such as programmer 14, may accomplish communication by RF communication techniques. In addition, telemetry module 70 may communicate with external medical device programmer 14 via proximal inductive interaction of IMD 16 with programmer 14. Accordingly, telemetry module 70 may send information to external programmer 14 on a continuous basis, at periodic intervals, or upon request from IMD 16 or programmer 14.

Power source 72 delivers operating power to various components of IMD 16. Power source 72 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
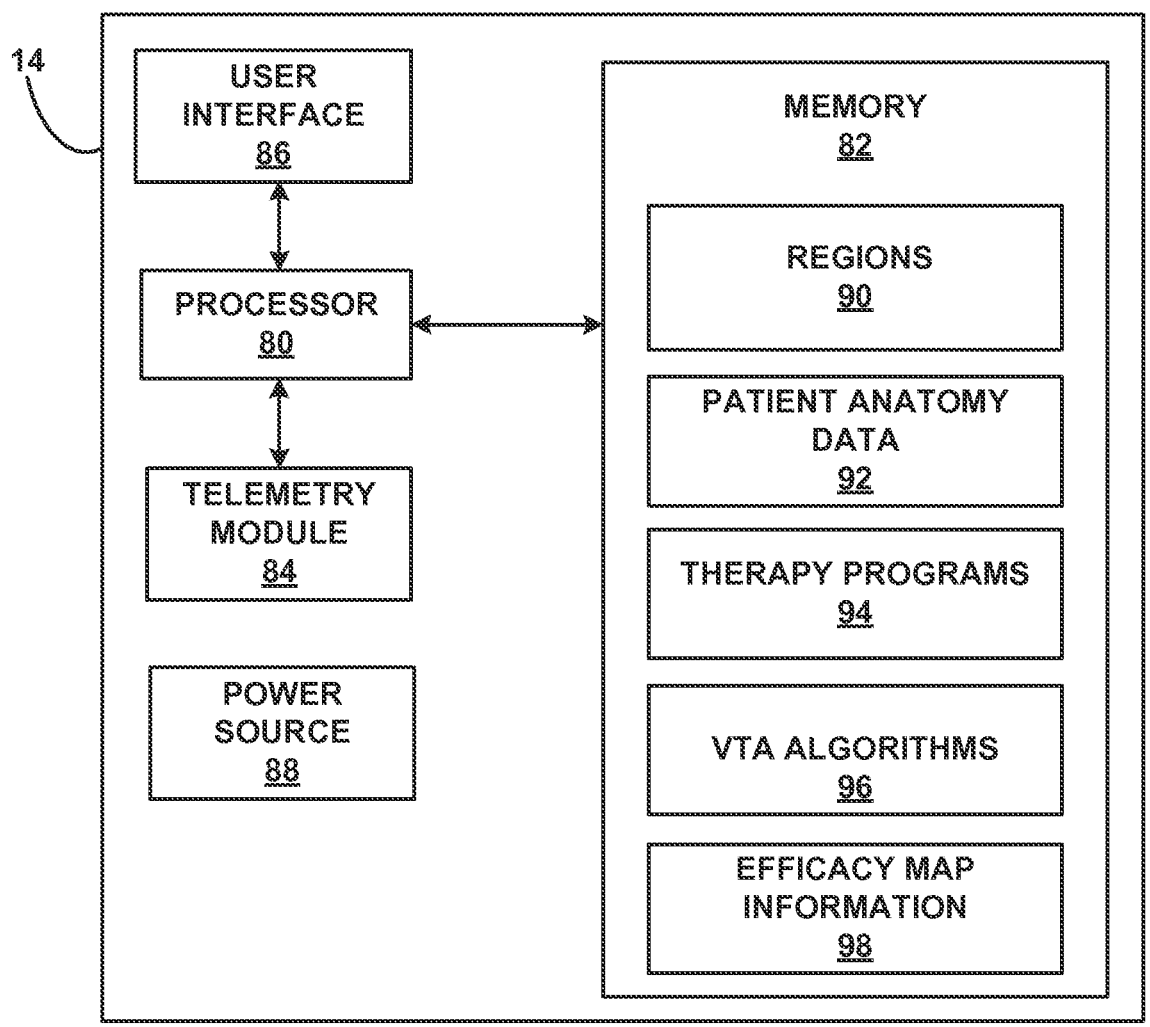
FIG. 3 is a functional block diagram illustrating components of an example medical device programmer.

FIG. 3 is a functional block diagram illustrating components of an example medical device programmer 14 (FIG. 1). Programmer 14 includes processor 80, memory 82, telemetry module 84, user interface 86, and power source 88. Processor 80 controls user interface 86 and telemetry module 84, and stores and retrieves information and instructions to and from memory 82. Programmer 14 may be configured for use as a clinician programmer or a patient programmer. Processor 80 may comprise any combination of one or more processors including one or more microprocessors, DSPs, ASICs, FPGAs, or other equivalent integrated or discrete logic circuitry. Accordingly, processor 80 may include any suitable structure, whether in hardware, software, firmware, or any combination thereof, to perform the functions ascribed herein to processor 80.

A user, such as a clinician or patient 12, may interact with programmer 14 through user interface 86. User interface 86 includes a display (not shown), such as a LCD or LED display or other type of screen, with which processor 80 may present information related to the therapy (e.g., electrodes and associated therapeutic windows). In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate though user interfaces presented by processor 80 of programmer 14 and provide input. In other examples, user interface 86 also includes audio circuitry for providing audible notifications, instructions or other sounds to patient 12, receiving voice commands from patient 12, or both.

Memory 82 may include instructions for operating user interface 86 and telemetry module 84, and for managing power source 88. In the example shown in FIG. 3, memory 82 also stores regions 90, patient anatomy data 92, therapy programs 94, VTA algorithms 96, and efficacy map information 98.

Regions 90 stores information identifying one or more regions of tissue of brain 28 (or another part of the body of the patient) associated with efficacious therapy delivery. These regions may be referred to as efficacy regions. Regions 90 also stores information identifying one or more regions of tissue of brain 28 (or another part of the body of patient) associated with adverse stimulation effects. These regions may be referred to as adverse-effects regions. The regions 90 may be identified using any suitable convention. In some examples, the efficacy and adverse-effects regions are identified by specific brain structures or parts of brain structures, coordinates of any suitable coordinate system to which leads 20 and brain 28 are registered, other anatomical structures, pixels of a two-dimensional (2D) grid to which brain 28 or another portion of the body of patient 12 is registered, voxels of a three-dimensional (3D) grid to which brain 28 or another portion of the body of patient 12 is registered (as discussed in further detail below), or any combination thereof.

The efficacy regions and adverse-effects regions stored by regions 90 may differ depending on the patient condition. For example, if therapy system 10 is implemented to manage tremors experienced by patient 12, regions 90 may include the substantia nigra because for some patients, stimulating the substantia nigra may help reduce the number and magnitude of tremors experienced by the patient.

In some examples, a clinician selects the stored regions 90. In other examples, the regions 90 are preselected and associated with a patient condition; processor 80 or a clinician may determine the regions 90 relevant to patient 12 by selecting the patient condition for which system 10 is implemented to manage.

Processor 80 is configured to generate a VTA for a particular set of stimulation parameter values, where the VTA represents the volume of tissue of patient 12 expected to be activated by the delivery, by a particular electrode (or combination of electrodes), of electrical stimulation to tissue of patient 12 according to the set of stimulation parameters. Processor 80 is configured to generate, for a particular electrode and a set of electrical stimulation parameter values, a VTA using VTA algorithms 96 and patient anatomy data 92 stored by memory 82 to generate the VTA. Patient anatomy data 92 may, for example, include the location of implanted electrodes 24, 26 in brain 28, the anatomical structure of patient 12, and the characteristics of the tissue, such as the impedance or neuron direction, proximate to implanted electrodes 24, 26. In examples in which the a target VTA has been generated before leads 20 are implanted in patient 12, patient anatomy data 92 may not include the actual location of implanted electrodes 24, 26 in brain 28, but, rather, a target location for electrodes 24, 26 in brain 28. Patient anatomy data 92 may be created from any type of imaging modality, such as, but not limited to, computed tomography (CT), magnetic resonance imaging (MRI), diffusion tensor imaging (DTI), x-ray, fluoroscopy, and the like.

VTA algorithms 96 may include one or more algorithms that processor 80 may implement to generate a VTA for a particular set of electrical stimulation parameter values and one or more active electrodes. When IMD 16 delivers electrical stimulation to tissue of patient 12 via an electrode (or combination of electrodes), an electrical field propagates away from the electrode. Processor 80 can implement the algorithms 96 to estimate which neurons will be activated by the electrical field propagating away from an electrode 24, 26 during the delivery of electrical stimulation by the electrode.

In some examples, the VTA algorithms 96 may include, for example, electrical field model equations that define how an electrical field propagates away from an origin location. In addition, VTA algorithms 96 may also include a set of equations, a lookup table, or another type of model that defines threshold action potentials of particular neurons that make up the anatomical structure, as defined by the patient anatomy data, affected by an electrical field. In some cases, this information may take into account an orientation of the neurons with respect to the electrical field. If the voltage or current amplitude of the electrical field is above the threshold action potential of any neuron within the electrical field, that neuron will be activated, e.g., cause a nerve impulse. Due to changes in electrical current propagation and threshold action potentials (e.g., a threshold voltage) required to activate a neuron, the activation of neurons may vary with the location of tissue around the lead. Some neurons may activate further from the lead with smaller voltages while other neurons may only be activated close to the lead because of a high voltage threshold and/or neuron orientation.

In some examples, memory 82 also stores information regarding the hardware characteristics of leads 20, and processor 80 generates the VTA based on the hardware characteristics. The hardware characteristics may include, for example, the number or types of leads 20 implanted within patient 12, the number of electrodes 24, 26, the size of each of the electrodes 324, 26, the type of electrodes 24, 26 (e.g., ring electrodes, partial-ring electrodes, segmented electrodes), and the like.

In some examples, processor 80 is configured to store determined efficacy maps in memory 82 as efficacy map information 98. A clinician may review the stored efficacy map information 98, e.g., during programming of IMD 16 to select one or more therapy programs with which IMD 16 may deliver efficacious electrical stimulation to patient 12. For example, the clinician may interact with user interface 86 to retrieve the stored efficacy map information 98. In other examples, the clinician may interact with user interface 86 to select between various stimulation parameter sets or electrode combination based on clinical ratings scores. In some examples, processor 80 is configured to generate and display a graphical user interface that indicates, for at least one electrode 24, 26 (e.g., each electrode 24, 26 or at least two electrodes 24, 26), the respective estimated clinical rating scale score. The clinician may then ascertain, relatively quickly, from the displayed information which electrodes have the highest estimated clinical rating scale score, which may be the electrodes associated with stimulation parameter values that are mostly likely to provide efficacious electrical stimulation therapy for patient 12.

In some examples, the clinician (or another user) may provide input via user interface 86 to manipulate a score, an efficacy score, a clinical rating scale score, or efficacy map information. For example, in response to receiving user input requesting the list of therapy programs be ordered by efficacy score, or estimated clinical rating scale score, processor 80 may reorganize the list of electrodes based on the efficacy score, the estimated clinical rating scale score, or a combination thereof (e.g., from large to small or vice versa). In some examples, the clinician may update efficacy map information 98 based on patient feedback.

Processor 80 may be configured to generate other types of interfaces. For example, processor 80 may be configured to generate a display including a list of a plurality electrodes combinations (e.g., each electrode combination may be assigned a unique alphanumeric identifier or a graphical identifier) ordered based on the associated efficacy scores or estimated clinical ratings scores without displaying the associated efficacy score or estimated clinical rating scale score. For example, the 5 electrode combinations with the highest associated efficacy score or estimated clinical rating scale score may be displayed. The clinician may then provide input via user interface 86 requesting additional information about a particular electrode combination. In response to receiving the user input, processor 80 may present another user interface with further details about the selected electrode combination, an efficacy score, an estimated clinical rating scale score, or a plurality of subscores.

In some examples, patient 12, a clinician or another user may interact with user interface 86 of programmer 14 in other ways to manually select therapy programs, generate new therapy programs, modify therapy programs, transmit the new programs to IMD 16, or any combination thereof.

Memory 82 may include any volatile or nonvolatile memory, such as RAM, ROM, EEPROM or flash memory. Memory 82 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 84. Accordingly, telemetry module 84 may be similar to the telemetry module contained within IMD 16. In other examples, programmer 14 may be capable of infrared communication or direct communication through a wired connection. In this manner, other external devices may be capable of communicating with programmer 14 without needing to establish a secure wireless connection.

Power source 88 is configured to deliver operating power to the components of programmer 14. Power source 88 may include a battery and a power generation circuit to produce the operating power. In some examples, the battery may be rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate.

Efficacy map information 98 may store one or more efficacy maps. In some examples, each efficacy map stored in efficacy map 98 may be associated with a different patient condition or symptom. In some examples, the efficacy maps may be clinical rating scale score efficacy maps (CRSEM), each associated with a particular patient condition or symptom. For example, efficacy map information 98 may include a CRSEM for each of a variety of clinical rating scales such as UPDRS, YBOCS and HDRS. The CRSEM information may be used to identify functional locations with brain 28. For example, the CRSEM information may include information regarding which areas of the brain provide the most therapeutic effect when activated for a particular condition. This information may be, for example, values associated with particular voxels within the CRSEM. In some examples, regions 90 may be taken into consideration when selecting a therapy program based on a CRSEM stored in efficacy map information 98 associated with a particular patient condition in scoring a therapy program. In some examples, a CRSEM may be used to generate a target VTA which may also be stored in efficacy map information 98.

While various information is shown stored in memory 82 of programmer 14, it will be understood that some or all of this information could alternatively or additionally be stored within memory 62 of IMD 16. As merely one example, raw or encoded patient anatomy data 92 may be stored within memory 62 of IMD 16 for portability. Moreover, at least some of the functionality ascribed to processor 80 of programmer 14 may instead or additionally be ascribed to processor 60 of IMD as discussed below.

Figure 4:
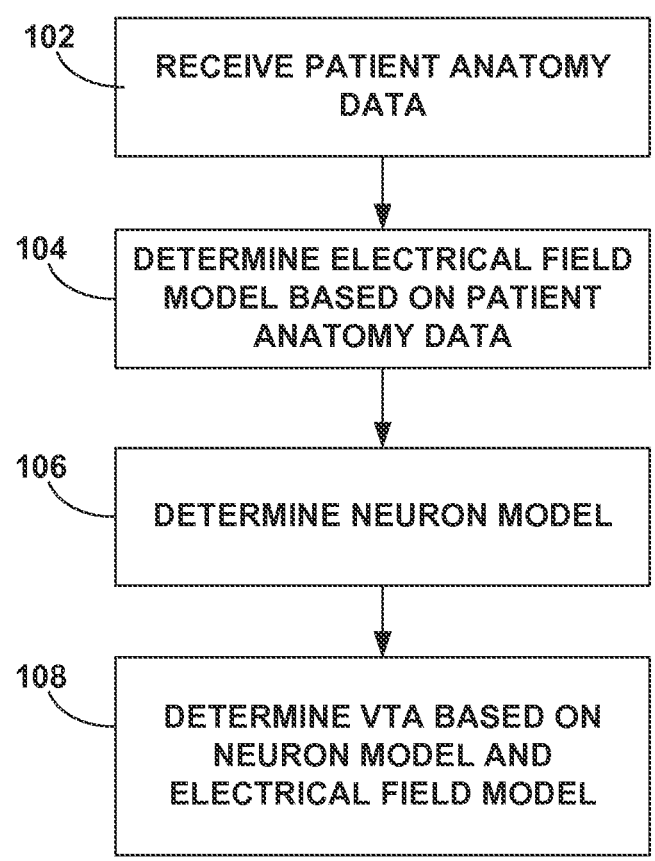
FIG. 4 is a flowchart illustrating an example method of generating a VTA.

FIG. 4 is a flow diagram of an example technique for determining a VTA. Although the technique of FIG. 4, as well as the techniques of FIGS. 5-9, is primarily described as being performed by processor 80 of programmer 14, in other examples, another processor, alone or in combination with processor 80, may perform any part of the techniques of FIGS. 4-9. For example, processor 60 of IMD 16 or a processor of another computing device alone or in combination with processor 80, may perform any part of the techniques of FIGS. 4-9.

In accordance with the technique shown in FIG. 4, processor 80 receives patient anatomy data necessary for creating an electrical field model (102). The patient anatomy data indicates one or more characteristics of tissue proximate the selected electrode. In some cases, this patient-specific data may be fitted to a standard anatomical atlas that represents anatomical structures, such as structures of the brain. The tissue proximate the selected electrode may be identified based on the known location of leads 20 within patient 12 or, if leads 20 are not implanted in patient 12, a target location of leads 20. For example, given a patient's MRI and post-operative CT scan, processor 80 can determine the position of lead 20 in brain 28 and, therefore, the anatomical structures proximate the implanted electrodes 24, 26. As another example, given a patient's MRI and post-operative CT scan, processor 80 can determine the anatomical structures proximate the target location of electrodes 24, 26 of leads 20, even if leads 20 have not yet been implanted in patient 12.

The patient anatomy data may be specific to or customized for patient 12, or may be more general (e.g., generic physical characteristics of human tissue applicable to a plurality of patients). In some examples, the patient anatomy data includes an anatomical image of target therapy delivery site within patient 12, a reference anatomical image, which may not be specific to patient 12, an anatomical atlas indicating specific structures of the patient's anatomy or a map of the tissue characteristics (e.g., conductivity or density) adjacent to electrodes 24, 26 of leads 20. The patient anatomy data may be created based on data generated by medical imaging, such as, but not limited to, CT, MRI, or any other volumetric imaging system. Processor 60 may store the patient anatomy data within section 92 of memory 82 (FIG. 3).

Processor 80 may model the effect of the electrical stimulation delivered by the selected electrode on tissue of patient 12. In the example shown in FIG. 4, processor 80 determines an electrical field model (104) that indicates the electrical field that will propagate away from the electrode when an electrical stimulation signal defined by the set of electrical stimulation parameter values is delivered by the electrode. Processor 80 may, for example, implement an algorithm (e.g., stored as a VTA algorithm 96 in memory 82 of programmer 14) to determine the electrical field model. The algorithm may take the received patient anatomy data into consideration, along with electrical field model equations that define electrical current propagation in order to determine how the electrical current will propagate away from the selected electrode.

Tissue variation within brain 28 (or other site within patient 12) may change the electrical current propagation from the electrode in some directions. These variations may contribute to varying VTA for electrodes 24, 26 of leads 20. Thus, the electrical field model equations take into consideration the physical tissue characteristics of the tissue adjacent electrodes 24, 26 of leads 20, which may be included in the patient anatomy data 92. That is, processor 80 determines the characteristics of the electrical field based on the actual anatomical structure and tissue characteristics of patient 12 being treated. From this information, processor 80 may estimate an electrical field that will be produced in therapy delivery via the selected electrode when IMD 16 generates an electrical stimulation signal in accordance with the set of electrical stimulation parameter values.

In another embodiment, a standard electric field model may be used that employs standard tissue characteristics for various types of tissues rather than determining an electrical field model that is based on patient-specific anatomy data. In such examples, processor 80 determines the characteristics (e.g., size, shape, and power distribution) of the electrical field based on generic physical characteristics of human tissue and known physical characteristics of the electrodes 24, 26 of leads 20. Thus, processor 80 may determine the electrical field model (which has already been pre-generated) by merely retrieving it from memory. In either example of using a patient-specific or more generic electric field model, the electrical field model may provide an approximation of what the electrical field would be in brain 28 of a specific patient 12. However, the electrical field model determined based on the actual anatomical structure of patient 12 may be a more accurate representation of the electrical field that will result from the delivery of electrical stimulation via the selected electrode.

In the technique shown in FIG. 4, processor 80 determines a neuron model (106). The neuron model indicates, for each of a plurality of volumes of tissue of patient 12, the voltage or current amplitude that is required for the tissue to be stimulated. For example, the neuron model may be a 3D grid of voxels, and each voxel may be associated with a voltage or current amplitude that is required for tissue within the particular voxel to be stimulated. As another example, the neuron model may include a grid of 2D areas, where each area of the grid may be associated with a voltage or current amplitude that is required for tissue within the particular area to be stimulated. In some examples, processor 80 determines the neuron model by generating the neuron model, e.g., based on tissue impedance characteristics of patient 12 determined using medical imaging and stored as patient anatomy data 92 (FIG. 3) or based on tissue impedance characteristics for a general atlas of brain 28. In other examples, processor 80 may determine the neuron model based on the geometries of brain fibers obtained from DTI imaging and stored as patient anatomy data 92 (FIG. 3). In other examples, the neuron model is predetermined by another processor and stored by memory 82 of programmer 14 (or another memory of another device); processor 80 may determine the neuron model by retrieving it from the memory. For example, the neuron model may be determined according to the techniques disclosed in U.S. Patent No. 2013/028966) to Molnar et al., filed Mar. 14, 2013, entitled "VISUALIZING TISSUE ACTIVATED BY ELECTRICAL STIMULATION", and incorporated herein by reference.

Processor 80 determines a volume of tissue activation (VTA) based on the electrical field model and the neuron model (108). The VTA may indicate which tissue of patient 12 will be activated (e.g., stimulated) by the electrical field expected to be generated from the delivery of electrical stimulation. In some examples, processor 80 determines the VTA by applying the neuron model to the electrical field determined by the electrical field model. The neuron model will indicate which neurons will be activated by the electrical field. The electrical field expected to result from delivery of electrical stimulation by the selected electrode and according to a particular set of electrical stimulation parameters may have an intensity too low to activate the neurons in at least some tissue proximate the selected electrode. Thus, by applying the neuron model to the electrical field determined by the electrical field model, processor 80 may determine the volume of tissue that is expected to be activated if electrical stimulation is delivered by the selected electrode to a target tissue location with specified electrical stimulation parameter values.

Figure 5:
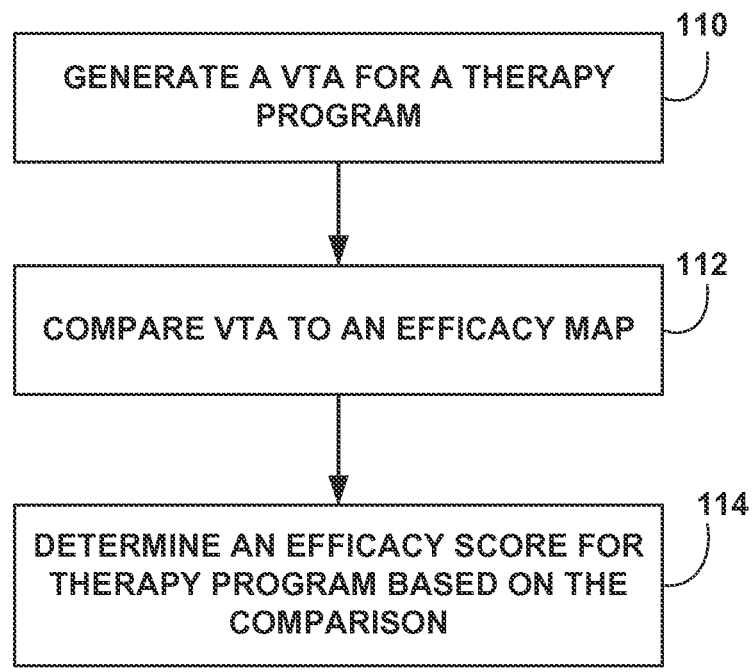
FIG. 5 is a flowchart illustrating an example method of generating an efficacy score for a VTA.

FIG. 5 is a flow diagram of an example technique for determining an efficacy score for a therapy program based on a VTA generated based on the therapy program. Processor 80 generates a volume of tissue activation (VTA) for a therapy program (110). The VTA may be generated based on VTA algorithms 96, and as discussed in further detail above with respect to FIG. 4. Processor 80 compares the generated VTA to an efficacy map (112). The efficacy map may be stored in efficacy map information 98. In some examples, processor 80 may select an efficacy map from efficacy map information 98 based on user input via user interface 86. For example, the efficacy map may be selected based on a symptom of patient 12 which is being treated. The user input may include, for example, an indication of the patient condition or one or more patient symptoms.

The efficacy map may include information regarding the regions of brain where stimulation is most efficacious at treating the symptom. In some examples, the efficacy map may be selected based on a patient condition. For example, for a patient condition which has a corresponding clinical rating scale, an efficacy map including values determined based on that clinical rating scale may be selected. An efficacy map incorporating a clinical rating scale may be a CRSEM. Clinical ratings scales which may be incorporated into efficacy maps include UPDRS, YBOCS, and HDRS, for example. Some clinical rating scales may include subscores directed to particular patient symptoms. In some examples, the CRSEM may include information regarding both an overall clinical rating scale score, and clinical rating scale scores for each subscores. The subscores may quantify the effect of a therapy program on a particular symptom or function. For example, the CRSEM may include subscores for speech, motor skills, movement, and tremor minimization. In other examples, an efficacy map for a particular condition may include information regarding which regions of the brain where stimulation is most efficacious at treating a plurality of symptoms associated with a particular condition. An efficacy map associated with a patient condition may incorporate a plurality of efficacy maps, one for each symptom being treated.

Processor 80 may register the generated VTA with a 3D grid using any suitable technique, such as by at least spatially transforming the generated VTA and 3D grid into a common coordinate system, e.g., thereby aligning the generated VTA with the volume of tissue represented by the 3D grid. For example, if the 3D grid represents the brain of patient 12, programmer 14 may rotate, scale, and translate the 3D grid, the generated VTA, or both, as needed, in order to substantially align the expected position of the generated VTA within brain 28 of patient 12 with the portion of the 3D grid corresponding to such a position. As a result, once registered, the relative position of the generated VTA and the 3D grid represents the expected position of the VTA within patient 12, e.g., within brain 28 of patient if the 3D grid represents brain 28. The 3D grid may be an efficacy map. In some examples, processor 80 compares the VTA and the efficacy map on a voxel by voxel basis for each voxel within the VTA. In other examples, processor 80 may compare the voxels around the perimeter of the VTA to the efficacy map. In some examples, a comparison to the efficacy map may be made based on a comparison of the generated VTA to a target VTA. For example, a target VTA may be generated which maximizes the efficacy of treatment based on the information in the efficacy map, as described in further detail below with respect to FIG. 9. The generated VTA may be compared to the target VTA on a voxel by voxel basis. In other examples, the generated VTA may be compared to the target VTA to determine the amount of overlap between the two VTAs.

Based on the comparison, processor 80 determines an efficacy score for the set of stimulation parameters (114). In some examples where the efficacy map is a CRSEM the efficacy score may be an estimated clinical rating scale score. In some examples the efficacy score may be based on how closely the VTA compares to a target VTA generated based on the efficacy map. The efficacy score may be used to quantify the relative effectiveness of a therapy program compared to a hypothetical therapy program which results in the target VTA, or the relative effectiveness of a therapy program with respect to other therapy programs. For example, the score may range from 0 to 100. In some examples, the score may be negative where, for example, the VTA indicates that stimulation according to the therapy program would result in a large number of adverse effects.

Processor 80 may use any suitable technique to determine the efficacy score. For example, the efficacy score may be a sum of the individual values (as defined by the efficacy map) for each voxel of the VTA, an average of the individual voxel values, a maximum voxel value, a minimum voxel value, a median voxel value, a percent of overlap between a target VTA and the generated VTA, or any other quantification of the relationship between the VTA and the efficacy map. In some examples, the efficacy score may be a sum of weighted subscores. For example, an efficacy score may be a sum of a subscore for desired effects on a patient's speech capabilities, and a subscore for undesired effects on a patient's swallowing capability, with the undesired effect on the patient's swallowing capability receiving twice as much weight as the desired effect on the patient's speech capabilities for purposes of arriving at the final overall efficacy score. In some examples, not shown, the technique of FIG. 5 may be repeated for a plurality of therapy programs. In some examples, not shown, the technique of FIG. 5 may also be repeated for a plurality of patient symptoms or conditions. In such examples processor 80 may determine the highest rated therapy program for each of the plurality of symptoms or conditions.

Figure 6:
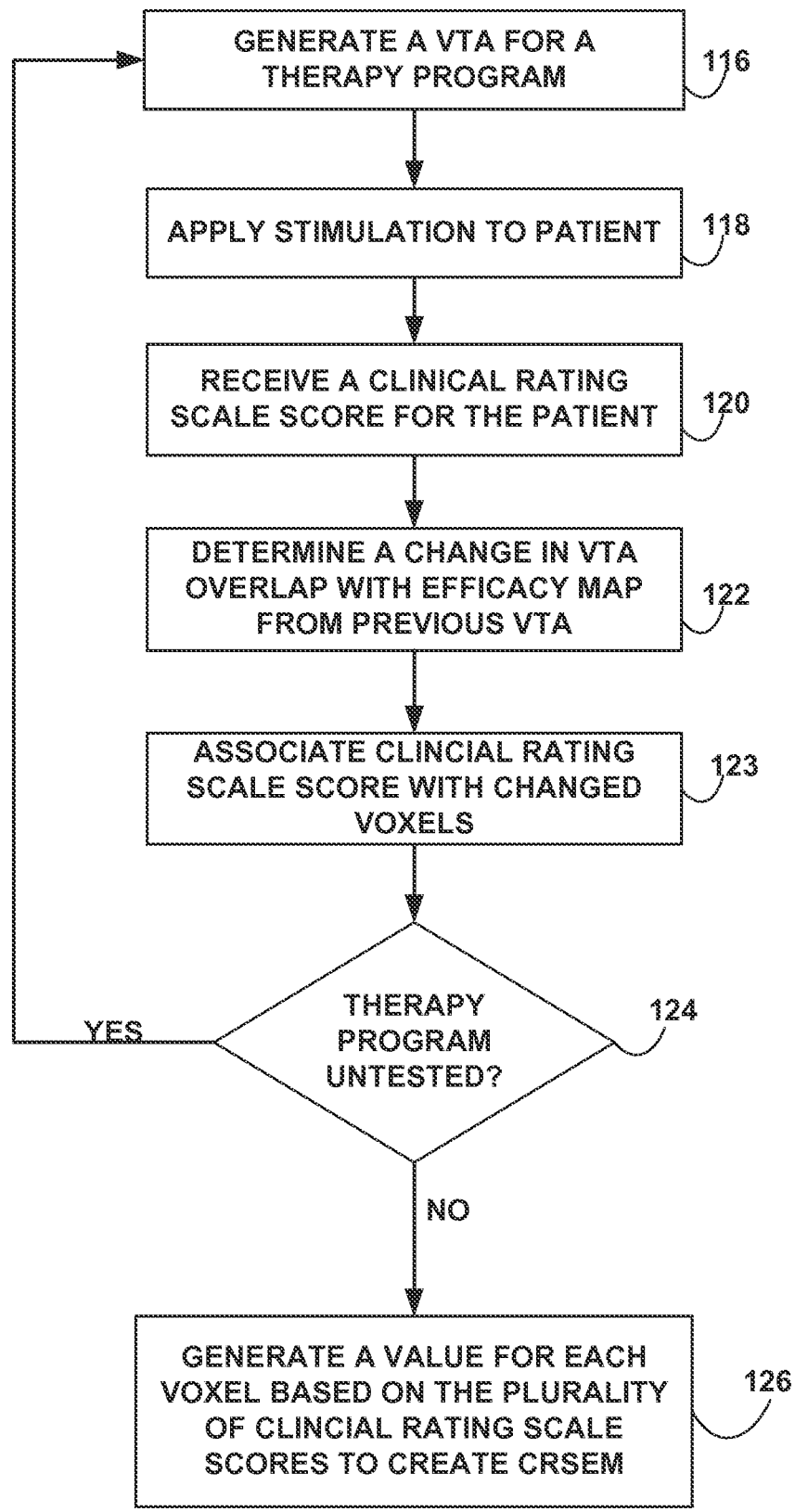
FIG. 6 is a flowchart illustrating an example method of generating a clinical rating scale efficacy map.

FIG. 6 is a flowchart illustrating an example method of determining the values assigned to voxels of an efficacy map. Processor 80 generates a volume of tissue activation for a therapy program (116). In some examples, the VTA may be generated based on VTA algorithms 96, and as discussed in further detail above with respect to FIG. 4. In some examples, processor 80 associates the generated VTA with regions of interest within brain 28 stored in regions 90. In other examples, the generated VTA may be associated with an efficacy map stored in efficacy map information 98. In some examples, the VTA may be associated with a brain atlas or efficacy map specific to patient 12. The association of the VTA with regions of interest or with an efficacy map may comprise registering the generated VTA to a 3D grid which represents the efficacy map. In some examples, the efficacy map may be a general efficacy map, and in other examples the efficacy map may be patient specific. For example, a patient-specific VTA may be registered to a 3D grid for a general efficacy map.

Processor 80 may register the generated VTA with the 3D grid using any suitable technique, such as by at least spatially transforming the generated VTA and 3D grid into a common coordinate system, e.g., thereby aligning the generated VTA with a volume represented by the 3D grid. For example, if the 3D grid represents the brain of patient 12, programmer 14 may rotate, scale, and translate the 3D grid, the generated VTA, or both, as needed, in order to substantially align the expected position of the generated VTA within brain 28 of patient 12 with the portion of the 3D grid corresponding to such a position. As a result, once registered, the relative position of the generated VTA and the 3D grid represents the expected position of the VTA within patient 12, e.g., within brain 28 of patient if the 3D grid represents brain 28.

Processor 80 controls IMD 16 to apply stimulation to patient 12 according to the therapy program (118). Processor 80 receives a clinical rating scale score for the patient (120) that results from the electrical stimulation therapy delivered by IMD 16 according to the therapy program. In some examples, a clinician determines the clinical rating scales score for the therapeutic effect of therapy applied to the patient according to the therapy program. In some examples, the clinician makes the determination while the therapy is being delivered to patient 12. In other examples, the determination may be made after the electrical stimulation is delivered to patient 12. The clinical rating scale score may be determined based on patient feedback. The clinical rating scale score may be a score characterizing the patient's condition based on a clinical rating scale such as UPDRS, YBOCS, or HDRS, for example. Processor 80 may receive the clinical rating scale score via user interface 86. For example, in a patient with Parkinson's disease, a clinician may evaluate mentation, behavior, mood, motor function, and daily activities such as speech and handwriting. In some examples, the evaluation may include patient feedback regarding certain daily activities. In some examples, the stimulation may be given over a period of time, during which the patient evaluates their current condition. Based on the evaluation, the clinician may assign a numeric score based on the UPDRS.

Processor 80 determines a change in VTA overlap with the efficacy map from the previous VTA (122). In some examples, processor 80 may determine both which voxels of the efficacy map are newly overlapped by the VTA and the voxels of the efficacy map that where previously overlapped by a VTA and are no longer overlapped by the current VTA. Processor 80 associates information related to the received clinical rating scale score with voxels of the efficacy map that were identified as changed (123). In some examples, if the clinical rating scale score has increased, then the received clinical rating scale score is associated with each voxel newly overlapped by the current VTA. Conversely, if the clinical rating scale score has decrease, the current VTA score may be associated with each of the voxels no longer overlapped by the current VTA. In some examples, processor 80 may also, or alternatively, determine a change in the clinical rating scale score between the previous VTA and the current VTA. The amount of change in the clinical rating scale score may be associated with each voxel which is different between the current VTA and the previous VTA within the efficacy map. In some examples, if the clinical rating scale score increased with respect to the previous VTA, then each voxel of the efficacy map newly overlapped by the VTA is associated with either the new clinical rating scale score, or a positive amount of change in the clinical rating scale score. Voxels that are no longer overlapped by the current VTA but which were overlapped by the previous VTA may be associated with a negative value corresponding to the amount of change in the clinical ratings scale score. In some example, processor 80 may associate the previous clinical rating scale score with the voxels that are no longer overlapped by the current VTA. In examples where the clinical rating scale score has decreased, processor 80 may associate a negative value corresponding to the change in clinical rating scale score with the voxels newly overlapped by the current VTA.

Processor 80 determines if there is a therapy program that is untested (124). In some examples, a predetermined number of therapy programs are tested. For example, values assigned to the voxels of the efficacy map may be determined based on a predetermined set of stimulation parameter value sets or therapy programs. In some examples, the predetermined therapy programs include at least one set of stimulation parameter values for each electrode combination of a plurality of electrode combinations. In some examples, the predetermined therapy programs to be tested may include multiple sets of stimulation programs for each electrode combination. For example, for each electrode combination, a therapy program resulting in a total energy of stimulation near a minimum total energy likely to activate one or more neurons in the areas around the active electrodes, and a second therapy program resulting in a total energy of stimulation near a maximum total energy IMD 16 is capable of producing may be part of the predetermined therapy programs. By determining values for each voxel of the efficacy map covering a range of therapy program parameters, processor 80 may be able to interpolate an efficacy score for a parameter value not tested during initial programming.

In other examples, therapy programs with one or more of the stimulation parameters incremented from a low parameter setting to a high parameter setting at a predetermined increment value may be tested. Each of the therapy programs to be tested may be predefined. In some examples, the programs may be entered by the clinician via programmer 14. In some examples, processor 80 may determine if there is an untested set of stimulation parameters by moving through a list of stimulation parameters sets.

If there is a set that has not been tested ("YES" branch of block 124), then processor 80 generates a new VTA for a different set of stimulation parameters (116), programmer 14 directs IMD 16 to apply electrical stimulation to patient 12 according to the new set of stimulation parameters (118), processor 80 receives a clinical rating scale score for the patient (120) that indicates the effects of the electrical stimulation therapy delivered according to the new set of parameters, and processor 80 associates the score with each voxel of the efficacy map overlapped by the VTA (122). This process may be repeated until each of the plurality of therapy programs has been tested.

Once all the stimulation parameter sets of the plurality have been tested ("NO" branch of block 124), processor 80 generates a value for each voxel based on the plurality clinical ratings scores associated with the voxel in order to create a CRSEM (126). The value describes the clinical benefit of activating the particular voxel. In some examples, the value is a combination of the clinical rating scale scores. For example, the value may be the average the clinical rating scale scores associated with a voxel. Other methods of describing the benefit may be the scores may include, for example, finding the maximum score, the minimum score, or the median score for each voxel. Another method of describing the benefit may be to assign to the voxel a score that is a logarithmic, exponential, or other non-linear function of the clinical rating scale score, such that, for example, voxels associated with higher clinical rating scale scores receive disproportionately higher voxel scores than voxels associated only with lower clinical rating scale scores. A CRSEM includes the values for each voxel. The CRSEM may be stored in efficacy map information 98. The stored CRSEM may be used later to generate an estimated clinical rating scale score for a selected therapy program based on the CRSEM, e.g., using the technique described with respect to FIG. 5. In some examples, the stored CRSEM may be used to generate a target VTA which corresponds to the highest possible estimated clinical rating scale score.

In some examples, the CRSEM stored in efficacy map information 98 is used to generate a clinical scale rating score for a therapy program for a patient different than the one used to generate the CRSEM. In some examples, the CRSEM information may be collected as part of a study and used, along with CRSEM information from additional patients, to generate a baseline CRSEM for use in other patients. In some examples, the CRSEM may be used to generate estimated clinical rating scale scores during follow-up or additional programming sessions for the same patient used to generate the CRSEM.

Figure 7:
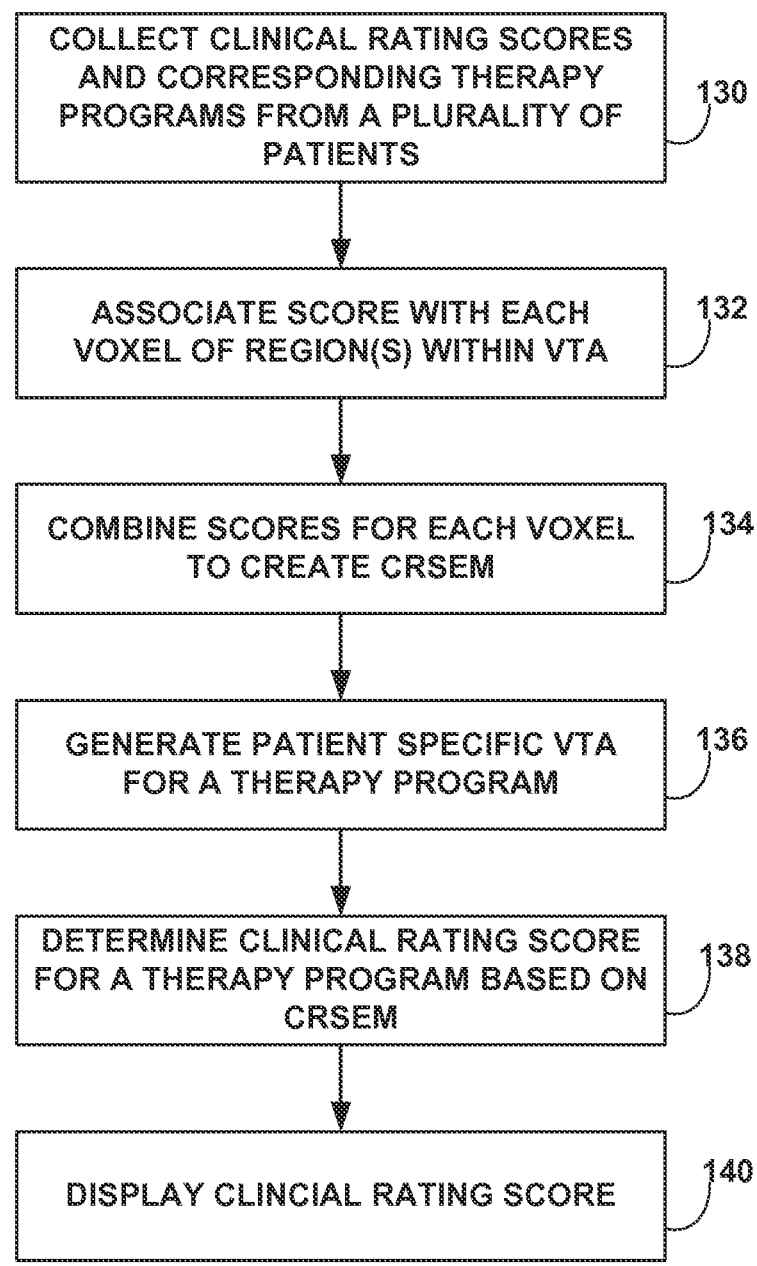
FIG. 7 is a flowchart illustrating an example method of determining an estimated clinical rating scale score for a therapy program.

FIG. 7 is a flowchart illustrating an example method of generating a CRSEM based on a plurality of patients, and generating an estimated clinical rating scale score based on the CRSEM. As described herein the CRSEM is generated using a programmer 14. However, in other examples, the CRSEM may be generated by another computing device and stored in efficacy map information 98 of the programmer. Although described with respect to a CRSEM, the method of FIG. 7 may be used to generate an efficacy map not associated with a particular clinical rating scale as well. A clinician or other user collects clinical rating scale scores and corresponding therapy programs from a plurality of patients (130). In examples in which the method of FIG. 7 is used to generate an efficacy map not associated with a clinical rating scale, the information collected quantifies the efficacy of a therapy program in some other way. For example, the information may quantify a difference in function between therapeutic programs. For each clinical rating scale score/therapy program combination, a processor, such as processor 80 of programmer 14, associates the score with each voxel of the efficacy map overlapped by VTA generated based on the therapy program (132). In some examples, the VTAs used to generate a general CRSEM may be generated using a general electrical field model as discussed above with respect to FIG. 4

Processor 80 combines the scores for each voxel to determine the values of the voxels and create a CRSEM (134). For example, processor 80 may determine the value of each voxel by determining the average score, the median score, the maximum score, or the minimum score for each voxel. In some examples, the maximum, minimum, and median score may all be associated with the voxel. The CRSEM is made up of the combined scores for each voxel. In some examples, multiple scores may be associated with a particular voxel. For example, a particular clinical rating scale may include subscales directed to particular symptoms of a disease. Each voxel may have an overall clinical rating scale score, as well as a score for each of the subscales associate with it. The CRSEM may be stored in efficacy map information 98.

After the CRSEM is generated, processor 80 generates a patient specific VTA for a set of stimulation parameters (136). The VTA may be generated according to the techniques discussed above with respect to FIG. 4. Processor 80 determines an estimated clinical rating scale score for the VTA based on the CRSEM (138). In some examples, the estimated clinical rating scale score is determined by comparing each voxel of the VTA to the CRSEM, and then generating the estimated clinical rating scale score based on the values associated with each voxel of the CRSEM that is overlapped by the VTA. The estimated clinical rating scale score may be computed by adding, averaging, or finding the maximum or minimum values of the voxels of the CRSEM with which the VTA overlaps, for example. Processor 80 may store the estimated clinical rating scale score in memory 82 or transmit the score to another device, or both.

In other examples, processor 80 determines the estimated clinical rating scale score by at least comparing the VTA generated based on a particular therapy program to a target VTA. The target VTA may be a VTA which results in the highest possible estimated clinical rating scale score from the CRSEM. The estimated clinical rating scale score for the patient specific VTA may be determined based on how closely the patient specific VTA aligns with the target VTA. For instance, if a certain percentage of the voxels of the patient specific VTA aligns with the target VTA, the patient specific VTA may be assigned a score that is this same percentage of the score associated with the target VTA.

In some examples, processor 80 displays the estimated clinical rating scale score to a user via a display of user interface 86 (140). The steps of generating a patient specific VTA (136) and determining an estimated clinical rating scale score (138) may be repeated for each of a plurality of stimulation parameter sets. In some examples, the programmer may display a single estimated clinical rating scale score. The estimated clinical rating scale score displayed may be the highest score achieved by each of the plurality of stimulation parameter sets tested. In some examples, the stimulation parameter set may be displayed along with the estimated clinical rating scale score. In some examples, a plurality of estimated clinical rating scale score/stimulation parameter set pairing may be displayed to a user. For example, stimulation parameter sets that maximize each of a plurality of subscores may also be displayed. In other examples, the highest estimated clinical rating scale score for each electrode combination, or a subset of electrode combinations, may be displayed. In some examples, a plurality of estimated clinical rating subscores score/parameter set combinations are displayed for a patient, who may select between stimulation parameters sets based on which symptom the patient would like to control the most. For example, a patient with Parkinson's may select one program while talking, and another program while walking.

Figure 8:
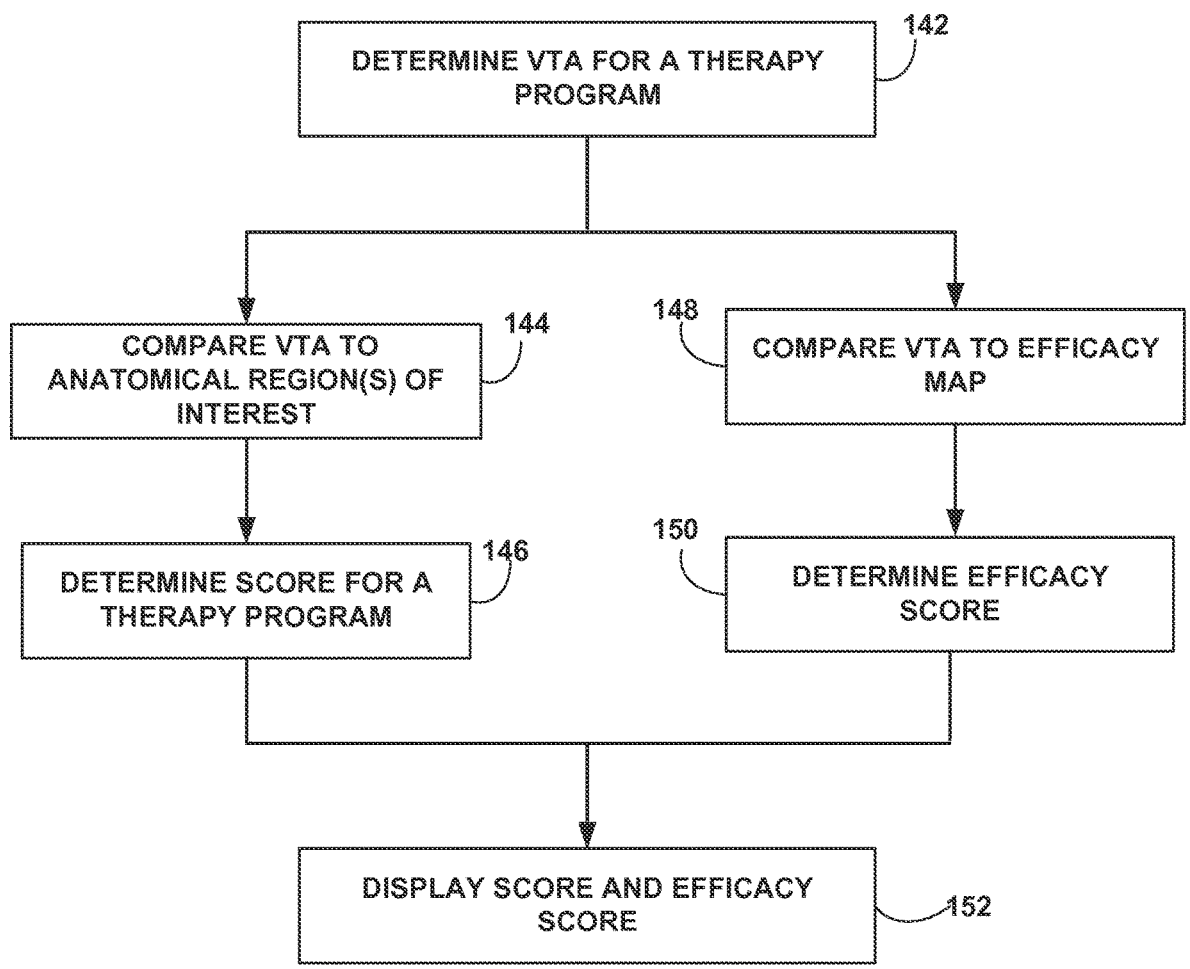
FIG. 8 is a flowchart illustrating an example technique for adjusting an anatomy-based score based on an efficacy score.

FIG. 8 is a flowchart illustrating an example technique displaying both a score based on anatomical region of interest and an efficacy score based on an efficacy map. Processor 80 determines a VTA for a set of stimulation parameters (142), e.g., using the technique discussed above with respect to FIG. 4. Processor 80 may generate two scores for the VTA: a score that indicates the overlap between the VTA and anatomical regions of interest, and an efficacy score which incorporates the function of each region of the brain and provides a number that may be either physiologically or clinically meaningful, as may be accomplished using an efficacy map. The efficacy score may be, for example, an estimated clinical rating scale score associated with a known clinical rating scale such as UPDRS, YBOCS, or HDRS. In other examples, the efficacy score may indicate the relative efficacy of stimulation parameter sets in treating a particular symptom or patient condition.

Processor 80 compares the VTA to anatomical regions of interest (144) stored in regions 90. The regions may be selected based on a patient condition, for example. In other examples, the regions may be selected based on location of lead 20. Processor 80 determines an anatomy-based score for the therapy program (146) based on the comparison. In some examples, the score may be a simple addition/subtraction calculation. For each voxel of the VTA which overlaps a desired region, processor 80 may increment the score 1 unit, and for each voxel which overlaps an undesired region, processor 80 may decrement the score is 1 unit. In some example, the amount of increment/decrement may change depending upon the region.

Processor 80 also compares the VTA to an efficacy map (148). The efficacy map quantifies how each voxel of the map contributes to the overall efficacy of a particular stimulation therapy. In some examples, the efficacy map may be a CRSEM. Processor 80 determines an efficacy score (150) for the therapy program based on the comparison. In examples where the efficacy map is a CRSEM, the efficacy score may be an estimated clinical rating scale score. Each voxel within the efficacy map may have a different value associated with it. In some examples, the combination of the individual values may be based on an efficacy map specific algorithm.

Programmer 14 may display the anatomy-based score and the efficacy score (152) to a user, such as a clinician or a patient. The display of both an anatomy-based score and an efficacy score may allow the clinician to gain confidence in the use of a scoring system the clinician is not familiar with. In addition, the display of both scores may enable the clinician to rely on previous experience using a programmer which displayed just one or the other type of scores. In some examples, the processor may select a stimulation program as most likely to provide appropriate treatment based on the score, while displaying the efficacy score to the user.

Figure 9:
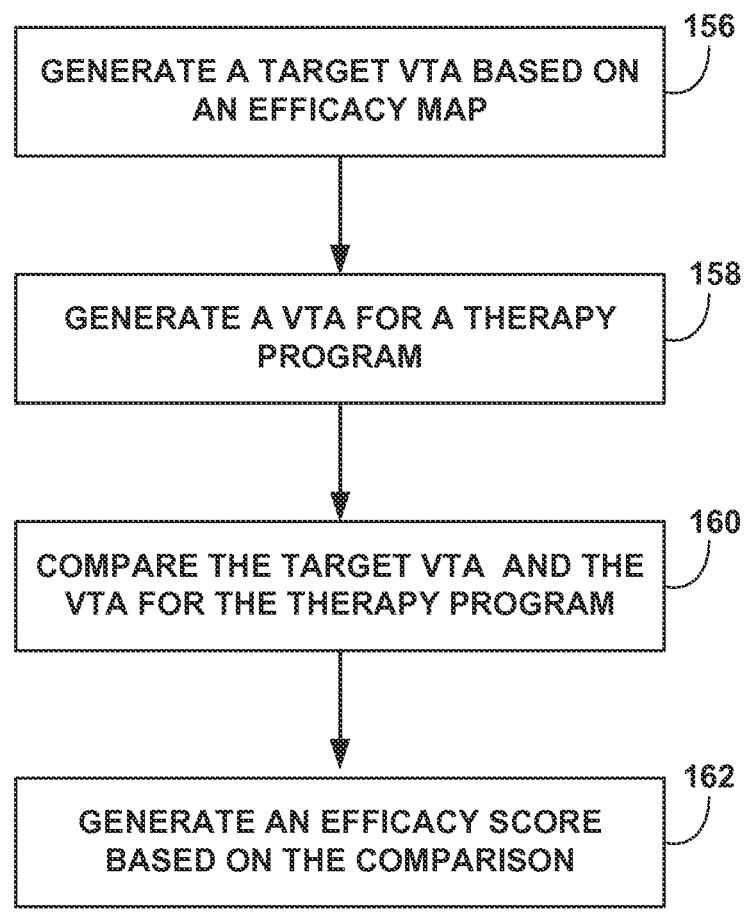
FIG. 9 is a flowchart illustrating an example technique of determining an efficacy score based on an efficacy map using a target VTA.

FIG. 9 is a flowchart illustrating an example technique of determining an efficacy score based on an efficacy map using a target VTA. Processor 80 generates a target VTA based on an efficacy map (156) stored in efficacy map information 98. In some examples, the target VTA may have been previously generated and stored in efficacy map information 98 along with the efficacy map. In order to generate the target VTA, processor 80 may identify a contiguous volume which results in a relatively high efficacy score (e.g., as indicated by a score greater than or equal to a stored efficacy score threshold) when scored against the efficacy map. In some examples, processor 80 generates the target VTA based on an algorithm which takes into account a variety of factors. For example, the algorithm may constrain the target VTA based on the amount of battery power used in generating the target VTA. In other examples, voxels outside the efficacy map, or with no value assigned, may be given a negative weight when determining the target VTA. In some examples, the algorithm for generating the target VTA may give additional weight to voxels with values above a certain threshold. In some examples, this volume may be constrained based on information regarding regions of the brain underlying the efficacy map. For example, if it is known that stimulation in one region will not propagate to another region of the brain, then processor 80 may implement an algorithm that limits the boundaries based on this information. The algorithm for generating the target VTA may attempt to encompass as many voxels of the efficacy map which positively affect the overall efficacy score, while avoiding voxels of the efficacy map which negatively affect the overall efficacy score and/or voxels not associated with a either a positive or negative effect on the overall efficacy score. In some examples, the algorithm used to generate the target VTA may constrain the target VTA to shapes that may be achieved using therapy programs and electrode configurations associated with IMD 16. For example, the target VTA may be constrained by shapes that may be achieved by therapy programs and electrode configurations currently programmed within the IMD 16. In some examples, the target VTA may be constrained by a larger set of available therapy programs and electrode configurations. In some examples, the target VTA may not be so limited, and may be unachievable using the therapy programs achievable by IMD 16. In some examples, processor 80 may also determine and save the efficacy score for the target VTA.

Processor 80 generates a VTA for a therapy program (158). The VTA may be generated using any suitable technique, including those discussed above with respect to FIG. 4. Processor 80 then compares the target VTA and the VTA for the therapy program (160). Processor 80 may register the generated VTA with the target VTA using any suitable technique, such as by at least spatially transforming the generated VTA and target VTA into a common coordinate system, e.g., thereby aligning the generated VTA with target VTA. For example, programmer 14 may rotate, scale, and translate the target VTA, the generated VTA, or both, as needed, in order to substantially align the expected position of the generated VTA and the brain 28 of patient 12 with the portion of the target VTA corresponding to such a position. Processor 80 generates an efficacy score based on the comparison (162) of the generated VTA to the target VTA. In some examples, processor 80 may compare the target VTA and the generated VTA on a voxel by voxel level and generate a score that indicates how closely the generated VTA aligns with the target VTA. For example, processor 80 may determine a percentage of overlap between the two VTAs. In some examples, processor 80 determines an estimated clinical rating score for the therapy program based on the percent of overlap between the target VTA and generated VTA. An estimated clinical rating score may be determined by multiplying the percent overlap by the estimated clinical rating score of the target VTA. In some examples, processor 80 may determine the number of voxels of the generated VTA within the target VTA and the number of voxels of the generated VTA outside the target VTA and increase a baseline score by a unit for each voxel within the target VTA and decrease the baseline score by a unit for each voxel outside the target VTA.

Processor 80 may determine a value that indicates how closely a VTA generated based on a particular therapy program aligns with (e.g., overlaps with) a target VTA for a plurality of therapy programs. Processor 80 may compare the values for the plurality of therapy programs and determine which therapy program most closely aligns with the target VTA. This therapy program may be considered the most efficacious therapy program and processor 80 may select the therapy program for programming chronic therapy delivery by IMD 16, or for further testing on patient 12. In some examples, processor 80 is configured to generate a graphical user interface that presents a plurality of therapy programs (e.g., by an identifier) and the respective values determined using the technique shown in FIG. 9.

While the techniques described above are primarily described as being performed by processor 60 of IMD 16 or processor 80 of programmer 14, in other examples, one or more other processors may perform any part of the techniques described herein alone or in addition to processor 60 or processor 80. Thus, reference to "a processor" may refer to "one or more processors." Likewise, "one or more processors" may refer to a single processor or multiple processors in different examples.

The techniques described in this disclosure, including those attributed to IMD 16, programmer 14, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored, as one or more instructions or code, on a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structures or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various examples of the disclosure have been described. These and other embodiments are within the scope of the following claims.

What is claimed is:

1. A method comprising: generating, by a processor and for each therapy program of a plurality of therapy programs, a volume of tissue activation (VTA) based on the respective therapy program; selecting an efficacy map from a plurality of stored efficacy maps based on a patient condition or a patient symptom, wherein each efficacy map of the plurality of efficacy maps comprises a plurality of voxels, each voxel being associated with a numerical value, wherein a first voxel of the plurality of voxels corresponds to a first volume of tissue associated with a positive result of tissue activation, the first voxel being associated with a first numerical value, and wherein a second voxel of the plurality of voxels corresponds to a second volume of tissue associated with the positive result of tissue activation, and the second voxel being associated with a second numerical value that is different from the first numerical value; for each therapy program of the plurality of therapy programs, determining, by the processor and based on one or more numerical values associated with one or more voxels of the plurality of voxels of the selected efficacy map and the respective VTA, an efficacy score for the therapy program with respect to the patient condition or the patient symptom; and transmitting, to a medical device, an indication of a selected therapy program that is selected from the plurality of therapy programs based on the efficacy score of the therapy program, the medical device delivering electrical stimulation therapy to a patient based on the selected therapy program in response to receiving the indication of the selected therapy program.

2. The method of claim 1, wherein at least one efficacy map of the plurality of stored efficacy maps is a clinical rating scale efficacy map (CRSEM), the CRSEM associated with a clinical rating scale.

3. The method of claim 2, wherein the CRSEM was generated retrospectively from information for a plurality of patients.

4. The method of claim 2, further comprising selecting the CRSEM as the efficacy map, wherein the efficacy score is an estimated clinical rating scale score.

5. The method of claim 2, wherein the clinical rating scale is one of: Unified Parkinson's Disease Rating scale, Yale-Brown Obsessive Compulsive Scale, or Hamilton Depression Rating Scale.

6. The method of claim 1, wherein selecting the efficacy map comprises selecting multiple efficacy maps from the plurality of stored efficacy maps, each of the selected efficacy maps being associated with a different patient symptom.

7. The method of claim 6, further comprising for each therapy program of the plurality of therapy programs, determining a plurality of efficacy scores based on the multiple efficacy maps; selecting a subset of the plurality of therapy programs based on the plurality of efficacy scores, wherein selecting the subset comprises selecting the therapy program of the plurality of therapy programs corresponding to the highest efficacy score for a particular patient symptom; and displaying the selected subset of the plurality of therapy programs.

8. The method of claim 1, wherein the selected therapy program is the therapy program of the plurality of therapy programs with the highest efficacy score.

9. The method of claim 8, wherein transmitting the indication of the selected therapy program comprises controlling the medical device to deliver therapy to the patient according to the selected therapy program.

10. The method of claim 1, further comprising: selecting a subset of therapy programs from the plurality of therapy programs based on the efficacy scores, wherein selecting the subset comprises selecting a subset of therapy programs comprising the therapy programs with the highest score for each electrode combination of a plurality of electrode combinations; and displaying each of the therapy programs within the subset.

11. A system comprising: a memory configured to store a plurality of efficacy maps; and a processor configured to: generate, for each therapy program of a plurality of therapy programs, a volume of tissue activation (VTA) based on the respective therapy program, select an efficacy map of the plurality of efficacy maps based on a patient condition or a patient symptom, wherein each efficacy map of the plurality of efficacy maps comprises a plurality of voxels, each voxel being associated with a numerical value, wherein a first voxel of the plurality of voxels corresponds to a first volume of tissue associated with a positive result of tissue activation, the first voxel being associated with a first numerical value, and wherein a second voxel of the plurality of voxels corresponds to a second volume of tissue associated with the positive result of tissue activation, and the second voxel being associated with a second numerical value that is different from the first numerical value, for each therapy program of the plurality of therapy programs, determine, based on one or more numerical values associated with one or more voxels of the plurality of voxels of the selected efficacy map and the respective VTA, an efficacy score for the therapy program with respect to the patient condition or the patient symptom; and transmit, to a medical device, an indication of a selected therapy program that is selected from the plurality of therapy programs based on the efficacy score of the therapy program, the medical device delivering electrical stimulation therapy to a patient based on the selected therapy program in response to receiving the indication of the selected therapy program.

12. The system of claim 11, wherein at least one of the plurality of efficacy maps is a clinical rating scale efficacy map (CRSEM), the CRSEM associated with a clinical rating scale.

13. The system of claim 12, wherein the CRSEM stored in the memory was generated retrospectively from information for a plurality of patients.

14. The system of claim 12, wherein the processor is further configured to select the CRSEM as the efficacy map, wherein the efficacy score is a clinical rating scale score.

15. The system of claim 12, wherein in the clinical rating scale is one of: Unified Parkinson's Disease Rating scale, Yale-Brown Obsessive Compulsive Scale, or Hamilton Depression Rating Scale.

16. The system of claim 11, wherein the processor is further configured to select multiple efficacy maps of the plurality of efficacy maps, each of the selected efficacy maps associated with a different patient symptom.

17. The system of claim 16, further comprising a user interface, wherein the processor is further configured to: for each therapy program of the plurality of therapy programs, determine a plurality of efficacy scores based on the multiple efficacy maps; select a subset of the plurality of therapy programs based on the plurality of efficacy scores, wherein selecting the subset comprises selecting the therapy program of the plurality of therapy programs corresponding to the highest efficacy score for a particular patient symptom; and display, via the user interface, each of the therapy programs within the subset.

18. The system of claim 11, wherein the selected therapy program is the therapy program of the plurality of therapy programs with the highest efficacy score.

19. The system of claim 18, further comprising the medical device and at least one electrode, wherein the processor is configured to transmit the indication of the selected therapy program by at least controlling the medical device to deliver therapy to the patient via the at least one electrode according to the selected therapy program.

20. The system of claim 11, further comprising a user interface, and wherein the processor is further configured to: select a subset of the plurality of therapy programs based on the efficacy scores, wherein selecting the subset of therapy programs comprises selecting a subset of therapy programs comprising the therapy programs with the highest score for each electrode combination of a plurality of electrode combinations; and display, via the user interface, each of the therapy programs within the subset.

21. A method comprising: generating, by a processor, and for each therapy program of a plurality of therapy programs, a volume of tissue activation (VTA) based on the respective therapy program; controlling a first medical device to deliver electrical stimulation to a patient according to each of the therapy programs; receiving a clinical rating scale score for the patient for each of the therapy programs; associating, by the processor, each clinical rating scale score with each voxel of an efficacy map overlapped by the VTA corresponding to the therapy program resulting in the clinical rating scale score; determining, by the processor, values for a plurality of voxels of the efficacy map based on the associated clinical rating scale scores, wherein determining the values comprises: determining a first numerical value for a first voxel of the plurality of voxels, the first voxel corresponding to a first volume of tissue associated with a positive result of tissue activation; and determining a second numerical value for a second voxel of the plurality of voxels, the second voxel corresponding to a second volume of tissue associated with the positive result of tissue activation, wherein the second numerical value is different from the first numerical value; storing, by the processor and in association with the efficacy map, the first numerical value for the first voxel and the second numerical value for the second voxel; and transmitting, to a second medical device, an indication of a selected therapy program that is selected from the plurality of therapy programs based on the first numerical value for the first voxel and the second numerical value for the second voxel, the second medical device delivering electrical stimulation therapy to a patient based on the selected therapy program in response to receiving the indication of the selected therapy program.

22. The method of claim 21, wherein determining the values for the plurality of voxels comprises, for a particular voxel of the plurality of voxels, combining the clinical rating scale scores associated with the particular voxel, to determine the value for the particular voxel.

23. A system comprising: a first medical device configured to deliver electrical stimulation to a patient according to each therapy program of a plurality of therapy programs; a user interface configured to receive a clinical rating scale score for the patient for each therapy program of the plurality of therapy programs; a memory; and a processor configured to: generate, for each therapy program of the plurality of therapy programs, a volume of tissue activations (VTA) based on the respective therapy program, associate each clinical rating scale score with each voxel of an efficacy map overlapped by the VTA corresponding to the therapy program resulting in the clinical rating scale score, determine values for the plurality of voxels of the efficacy map based on the associated clinical rating scale scores, wherein the processor is configured to determine the values by at least determining a first numerical value for a first voxel of the plurality of voxels, the first voxel corresponding to a first volume of tissue associated with a positive result of tissue activation, and determining a second numerical value for a second voxel of the plurality of voxels, the second voxel corresponding to a second volume of tissue associated with the positive result of tissue activation, wherein the second numerical value is different from the first numerical value; store, in the memory and in association with the efficacy map, the first numerical value for the first voxel and the second numerical value for the second voxel; and transmit, to a second medical device, an indication of a selected therapy program that is selected from the plurality of therapy programs based on the first numerical value for the first voxel and the second numerical value for the second voxel, the second medical device delivering electrical stimulation therapy to a patient based on the selected therapy program in response to receiving the indication of the selected therapy program.

24. The system of claim 23, wherein the processor is configured to determine the values for the plurality of voxels by at least combining, for a particular voxel of the plurality of voxels, the clinical rating scale scores associated with the particular voxel, to determine the value for the particular voxel.

25. The method of claim 1, wherein determining, by the processor and based on the one or more numerical values associated with the one or more voxels of the plurality of voxels of the selected efficacy map and the VTA, the efficacy score for the therapy program with respect to the patient condition or the patient symptom comprises: registering, by the processor, the VTA with the selected efficacy map; after registering the VTA with the selected efficacy map, determining, by the processor, the one or more voxels of the plurality of voxels of the efficacy map with which the VTA overlaps; and determining, by the processor, at least one of a sum, an average, a maximum, a minimum, or a median of the one or more numerical values associated with the one or more voxels with which the VTA overlaps.

26. The system of claim 11, wherein the processor is configured to determine, based on the one or more numerical values associated with the one or more voxels of the plurality of voxels of the selected efficacy map and the VTA, the efficacy score for the therapy program with respect to the patient condition or the patient symptom by at least: registering the VTA with the selected efficacy map, after registering the VTA with the selected efficacy map, determining the one or more voxels of the plurality of voxels of the efficacy map with which the VTA overlaps, and determining at least one of a sum, an average, a maximum, a minimum, or a median of the one or more numerical values associated with the one or more voxels with which the VTA overlaps.

27. The method of claim 1, wherein the first and second numerical values are each associated with the positive result of tissue activation.

28. The method of claim 27, wherein the positive result of tissue activation comprises a first positive result of tissue activation and a second positive result of tissue activation different from the first positive result, and wherein the first volume of tissue is associated with the first positive result of tissue activation and the second volume of tissue is associated with the second positive result of tissue activation.

29. The method of claim 1, wherein transmitting the indication of the selected therapy program comprises controlling the medical device to deliver the electrical stimulation therapy to the patient according to the selected therapy program.

30. The system of claim 11, further comprising the medical device and at least one electrode, wherein the processor is configured to transmit the indication of the selected therapy program by at least controlling the medical device to deliver the electrical stimulation therapy to the patient via the at least one electrode according to the selected therapy program.

31. The method of claim 1, wherein the indication of the selected therapy program comprises programming information for programming the medical device to deliver therapy according to the selected therapy program.

32. The method of claim 1, wherein the indication of the selected therapy program indicates one or more electrical stimulation therapy parameter values of the selected therapy program.

33. The system of claim 11, wherein the indication of the selected therapy program comprises programming information for programming the medical device to deliver therapy according to the selected therapy program.

34. The system of claim 11, wherein the indication of the selected therapy program indicates one or more electrical stimulation therapy parameter values of the selected therapy program.

* * * * *